US011246881B2

(12) United States Patent
Smith et al.

(10) Patent No.: US 11,246,881 B2
(45) Date of Patent: Feb. 15, 2022

(54) NANOPARTICLE TO TARGET CANCER

(71) Applicants: Georgetown University, Washington, DC (US); The United States of America, as represented by the Secretary, Department of Health & Human Services, Bethesda, MD (US)

(72) Inventors: Jill P. Smith, Washington, DC (US); Stephan Stern, Frederick, MD (US); Abdullah Mahmud, Frederick, MD (US)

(73) Assignees: The United States of America, as represented by the Secretary, Department of Health and Human Services, Bethesda, MD (US); Georgetown University, Washington, DC (US)

(*) Notice: Subject to any disclaimer, the term of this patent is extended or adjusted under 35 U.S.C. 154(b) by 95 days.

(21) Appl. No.: 16/084,942

(22) PCT Filed: Mar. 15, 2017

(86) PCT No.: PCT/US2017/022567
§ 371 (c)(1),
(2) Date: Sep. 13, 2018

(87) PCT Pub. No.: WO2017/161031
PCT Pub. Date: Sep. 21, 2017

(65) Prior Publication Data
US 2019/0076457 A1 Mar. 14, 2019

Related U.S. Application Data

(60) Provisional application No. 62/309,250, filed on Mar. 16, 2016.

(51) Int. Cl.
| | |
|---|---|
| *C07H 21/02* | (2006.01) |
| *A61K 48/00* | (2006.01) |
| *A61K 31/7088* | (2006.01) |
| *C12N 15/115* | (2010.01) |
| *A61K 47/10* | (2017.01) |
| *A61K 47/18* | (2017.01) |
| *A61K 9/107* | (2006.01) |
| *A61K 9/51* | (2006.01) |
| *C12N 15/11* | (2006.01) |
| *A61K 47/60* | (2017.01) |
| *A61K 47/64* | (2017.01) |
| *A61K 47/69* | (2017.01) |
| *A61K 31/713* | (2006.01) |
| *A61P 35/00* | (2006.01) |
| *A61K 9/127* | (2006.01) |
| *B82Y 5/00* | (2011.01) |

(52) U.S. Cl.
CPC ........ *A61K 31/7088* (2013.01); *A61K 9/1075* (2013.01); *A61K 9/127* (2013.01); *A61K 9/5146* (2013.01); *A61K 31/713* (2013.01); *A61K 47/10* (2013.01); *A61K 47/183* (2013.01); *A61K 47/60* (2017.08); *A61K 47/6455* (2017.08); *A61K 47/6935* (2017.08); *A61P 35/00* (2018.01); *B82Y 5/00* (2013.01); *C12N 15/111* (2013.01); *C12N 15/115* (2013.01); *C12N 2310/14* (2013.01); *C12N 2310/16* (2013.01); *C12N 2310/351* (2013.01); *C12N 2320/30* (2013.01); *C12N 2320/32* (2013.01)

(58) Field of Classification Search
CPC ... A61K 47/60; C12N 2310/14; C12N 15/113
See application file for complete search history.

(56) References Cited

U.S. PATENT DOCUMENTS

| | | | |
|---|---|---|---|
| 8,153,110 B2 | 4/2012 | Kataoka et al. | |
| 8,889,640 B1 | 11/2014 | Smith et al. | |
| 9,149,544 B2 | 10/2015 | Morgan et al. | |
| 2009/0053169 A1 | 2/2009 | Castillo et al. | |

FOREIGN PATENT DOCUMENTS

| | | |
|---|---|---|
| WO | WO 01/09163 | 2/2001 |
| WO | WO 2011/057216 | 5/2011 |

OTHER PUBLICATIONS

Elbashir et al. (The EMBO Journal, vol. 20, No. 23, pp. 6877-6888, 2001).*
Wang et al. (World J Gastroenterol, 2005, 11(13):2026-2031).*
Burks et al., "High Throughput Screening and Natural Products," poster presentation, AACR Apr. 18, 2016.
International Search Report and Written Opinion issued for International Application No. PCT/US2017/022567 dated Jun. 25, 2017.
Kim et al., "Precise engineering of siRNA delivery vehicles to tumors using polyion complexes and gold nanoparticles," *ACS Nano*, 8(9): 8879-8991, Aug. 18, 2014.
Mahmud et al., "Development of Targeted Polyethylene Glycol-poly(L-Lysine) Polyplex for the Delivery of siRNA to Pancreatic Cancer," abstract, AAPS Oct. 1, 2015.
Matters et al., "Growth of Human Pancreatic Cancer is Inhibited by Down-Regulation of Gastrin Gene Expression," *Pancreas*, 38(5): E151-E161, Jul. 2009.

(Continued)

*Primary Examiner* — Amy H Bowman
(74) *Attorney, Agent, or Firm* — Klarquist Sparkman, LLP

(57) ABSTRACT

A construct, or a pharmaceutically acceptable salt thereof, comprising:
(a) a polyethylene glycol-block-poly(L-lysine) polymer moiety, wherein the polyethylene glycol is thiol-functionalized;
(b) a cholecystokinin-B (CCK-B) receptor ligand coupled to the polyethylene glycol of the polymer moiety; and
(c) a siRNA complexed with the poly(L-lysine) of the polymer moiety,
wherein the construct is neutralized.

33 Claims, 20 Drawing Sheets
Specification includes a Sequence Listing.

(56) References Cited

OTHER PUBLICATIONS

Sharma et al., "Bioconjugation of Calcium Phosphate Nanoparticles for Selective Targeting of Human Breast and Pancreatic Cancers In Vivo," *ACS Nano*, 4(3): 1279-1287, Mar. 23, 2010.
Zhu et al. "Progress in aptamer-mediated drug delivery vehicles for cancer targeting and its implications in addressing chemotherapeutic challenges," *Theranostics*, 4(9): 931-944, Jul. 13, 2014.
Smith et al., "Cholecystokinin and pancreatic cancer: the chicken or the egg?" *Am J Physiol Gastrointest Liver Physiol*, 306(2): G91-G101, Jan. 15, 2014.
Smith et al., "Cholecystokinin receptor antagonist halts progression of pancreatic cancer precursor lesions and fibrosis in mice," *Pancreas*, 43(7): 1050-1059, Oct. 2014.
Smith et al., "Cholecystokinin receptors and PANC-1 human pancreatic cancer cells," *Am J Physiol Gastrointest Liver Physiol*, 265(1): G149-G155, Jul. 1993.
Smith et al., "Identification and characterization of CCK-B/gastrin receptors in human pancreatic cancer cell lines," *Am J Physiol Gastrointest Liver Physiol*, 266(1): R277-R283, Jan. 1994.
"Pennsylvania State University Annual Progress Report: 2012 Formula Grant," Report prepared by Pennsylvania Department of Health and Pennsylvania State University, 2012.
Burks et al., "Cholecystokinin receptor-targeted polyplex nanoparticle inhibits growth and metastasis of pancreatic cancer," *CMGH*, 6(1): 17-32, Mar. 7, 2018.
Clawson et al., "A cholecystokinin B receptor-specific DNA aptamer for targeting pancreatic ductal adenocarcinoma," *Nucleic Acid Therapeutics*, 27(1): 23-36, Feb. 1, 2017.
Extended European Search Report issued for EPC Application No. 17767463 dated Jan. 15, 2020.
Oe et al., "Actively-targeted polyion complex micelles stabilized by cholesterol and disulfide cross-linking for systemic delivery of siRNA to solid tumors," *Biomaterials*, vol. 35, pp. 7887-7895, Jun. 13, 2014.
Patil et al., "Multifunctional triblock nanocarrier (PAMAM-PEG-PLL) for the efficient intracellular siRNA delivery and gene silencing," *ACS Nano*, 5(3): 1877-1887, Feb. 15, 2011.

\* cited by examiner

FIG. 4A
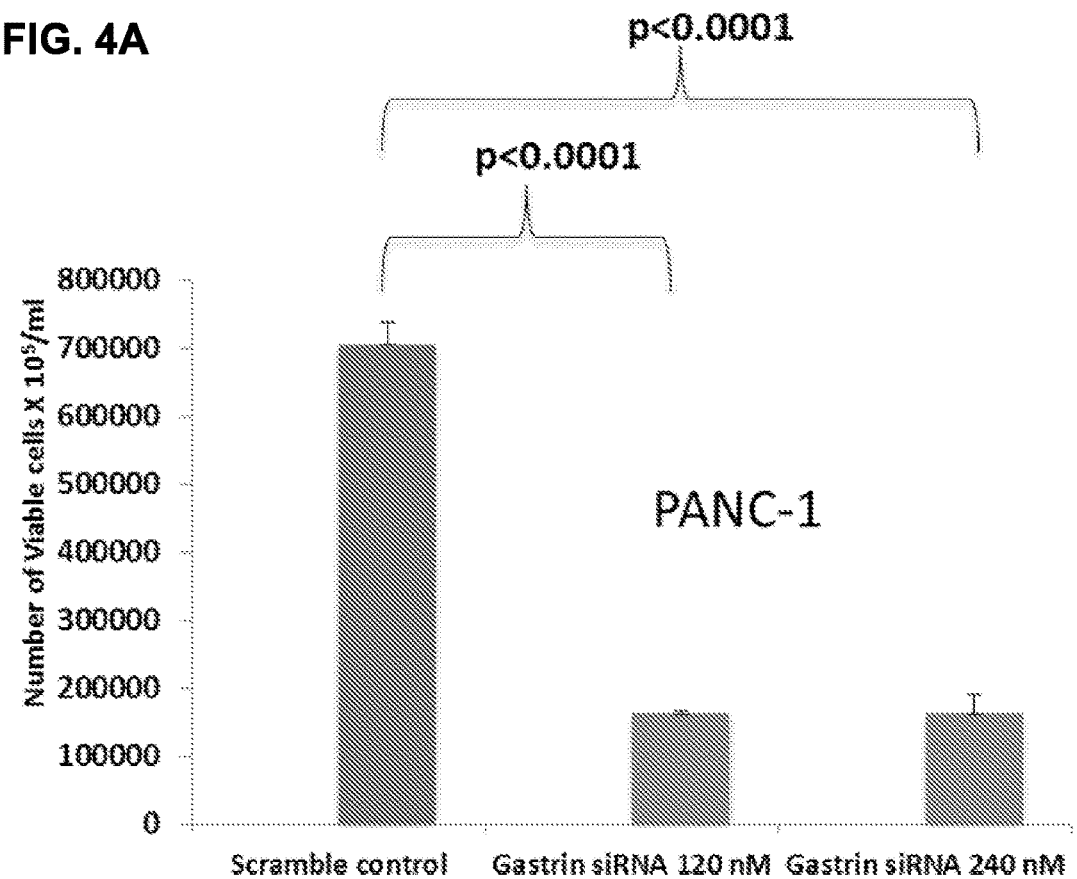
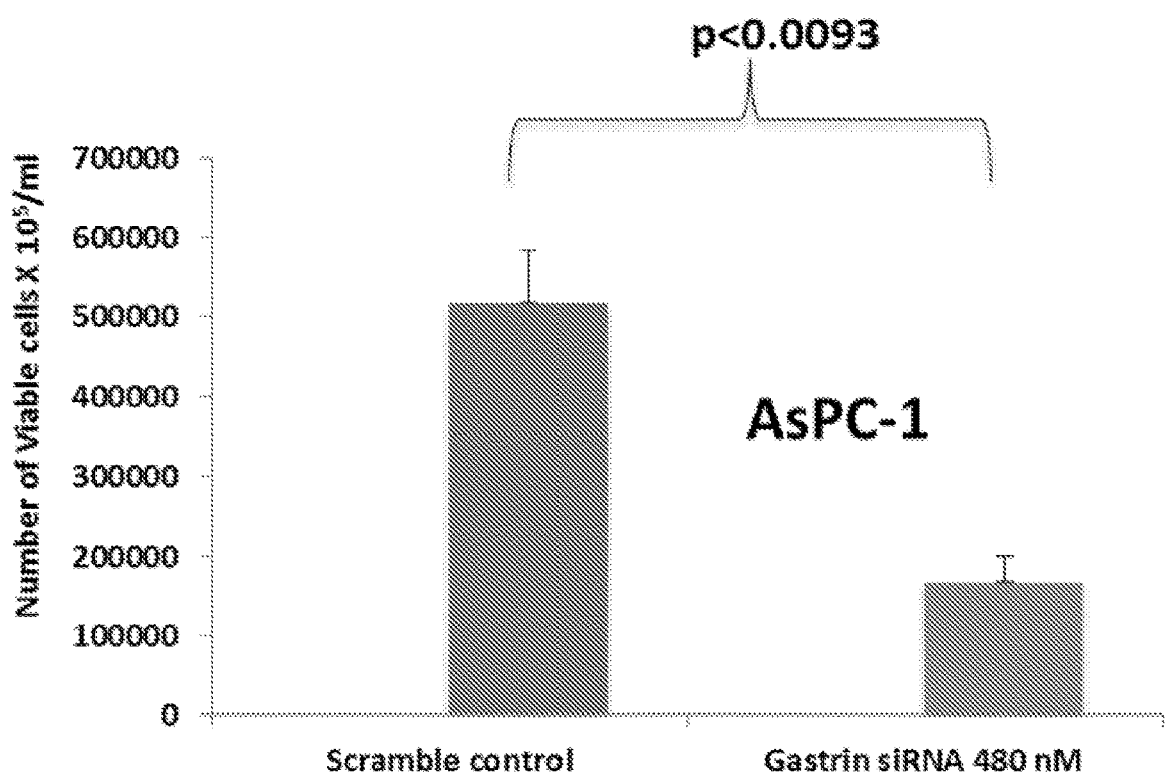

FIG. 4B  FIG. 4C  FIG. 4D
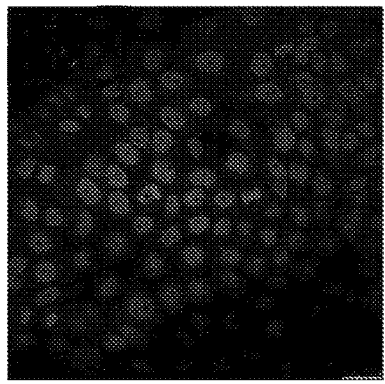
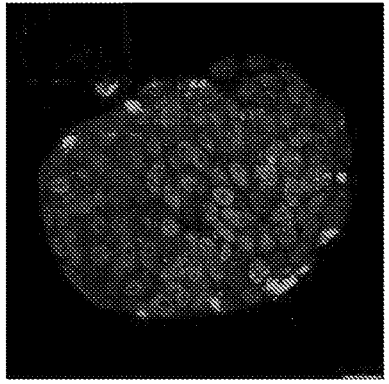
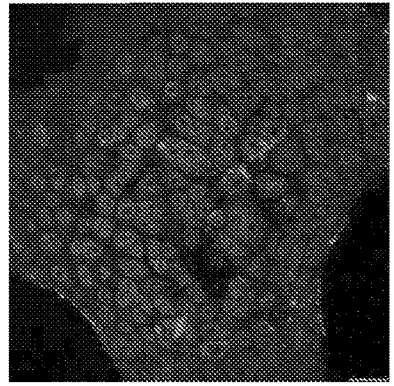
FIG. 4E
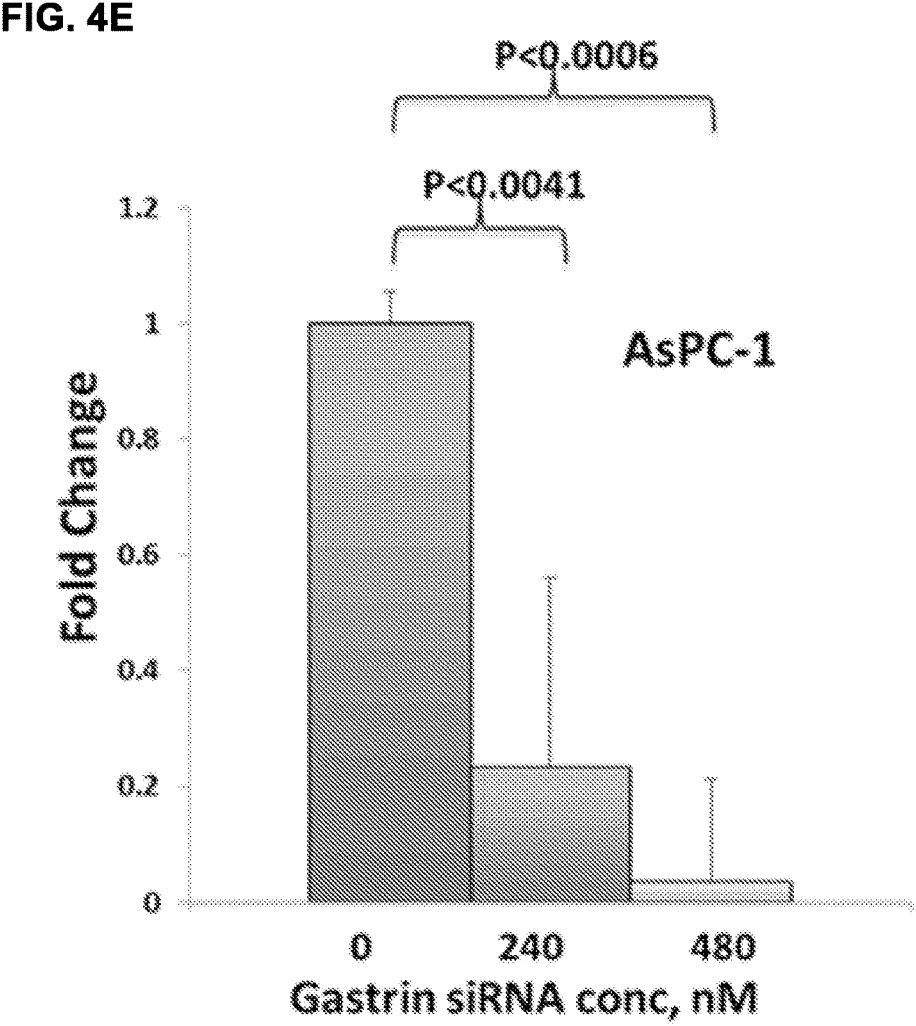

FIG. 4F
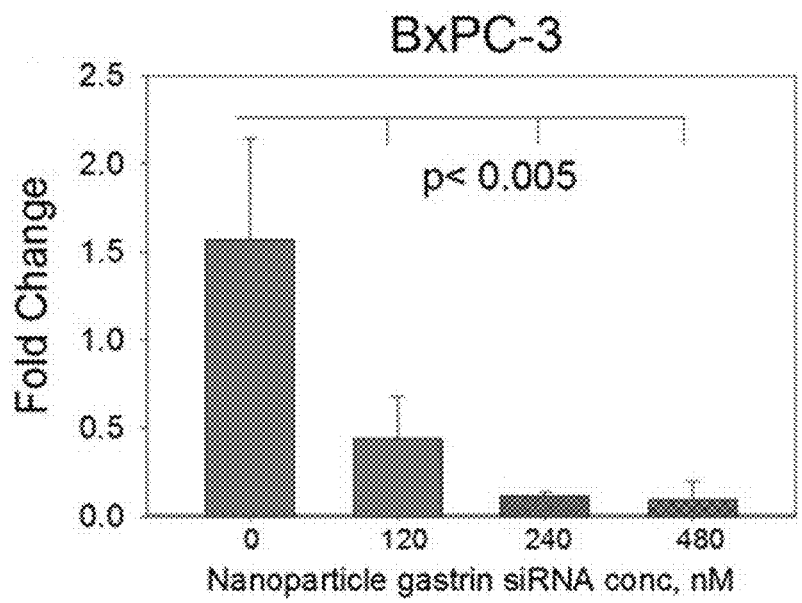
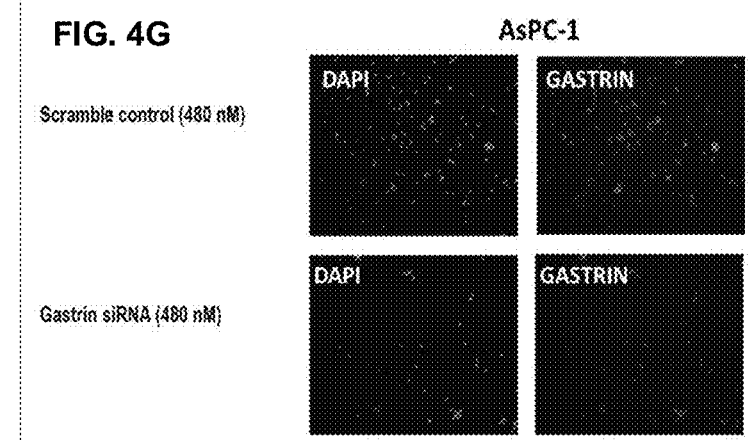
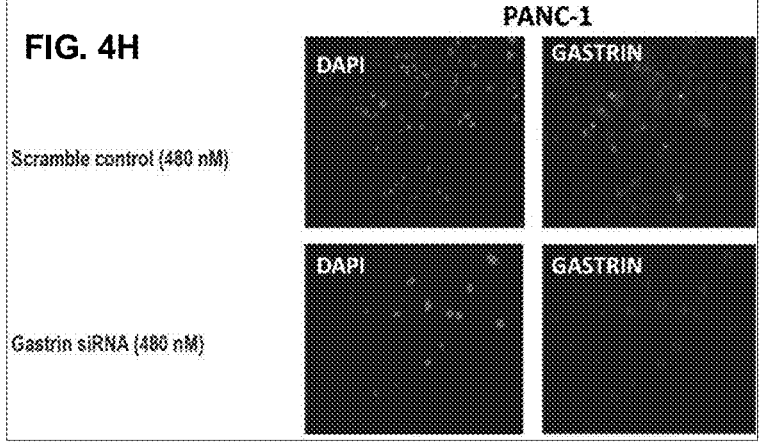

FIG. 6A      FIG. 6B
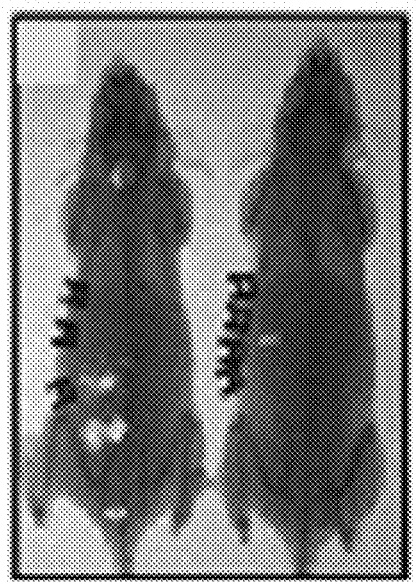 
FIG. 7
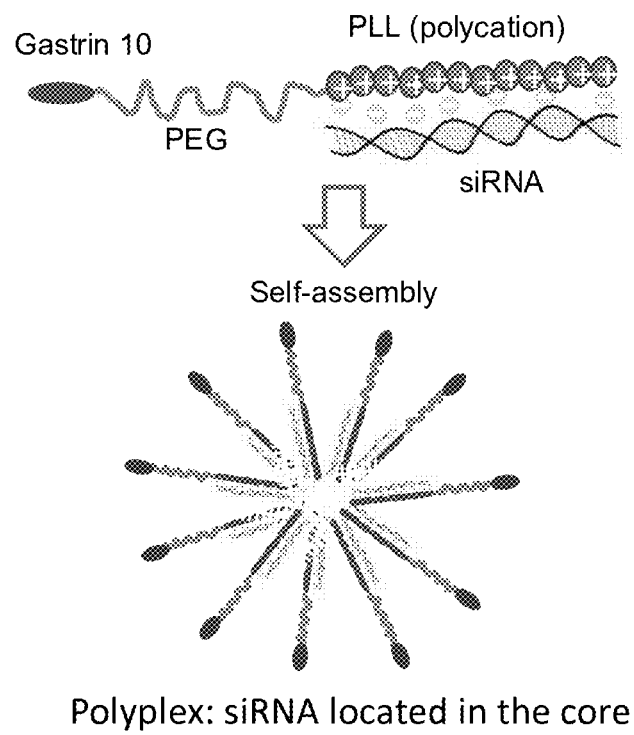
Polyplex: siRNA located in the core

FIG. 12B
Deprotection of trityl group and SH-PEG-PLL: $^1$H nmr
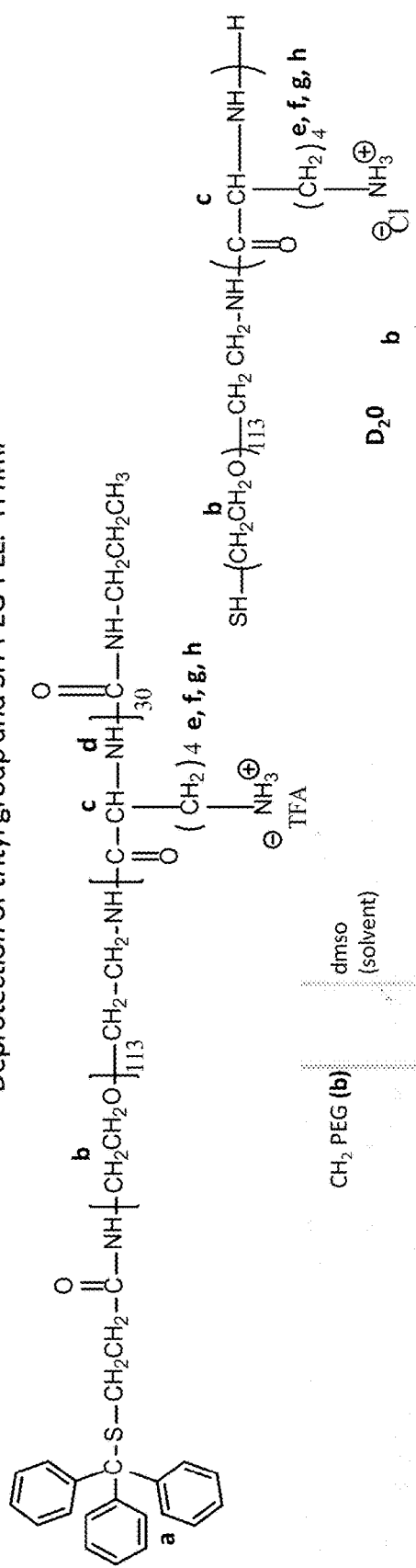
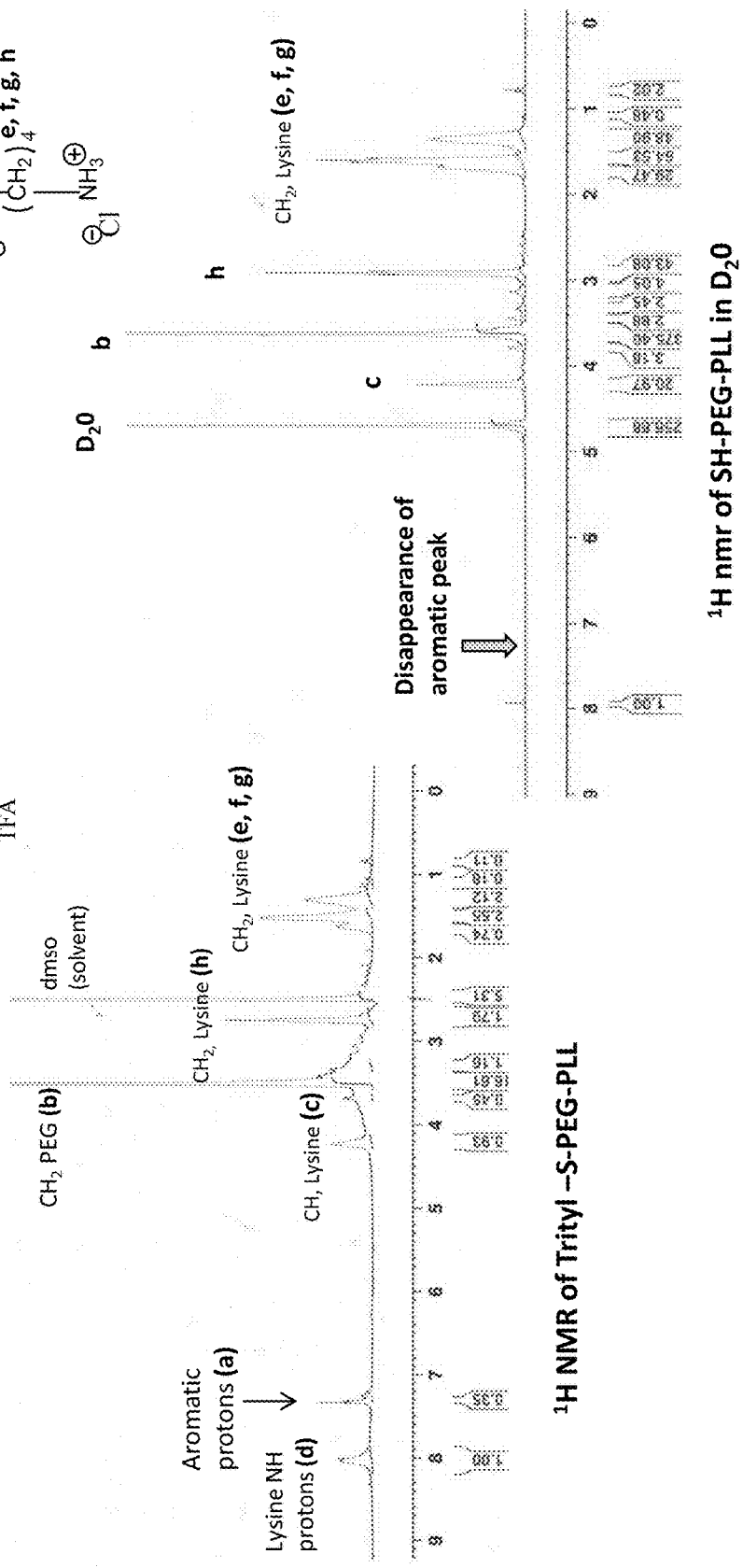

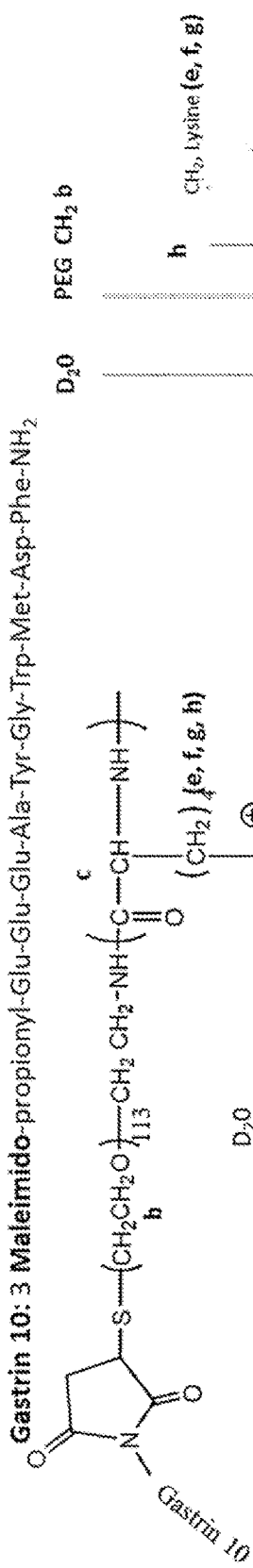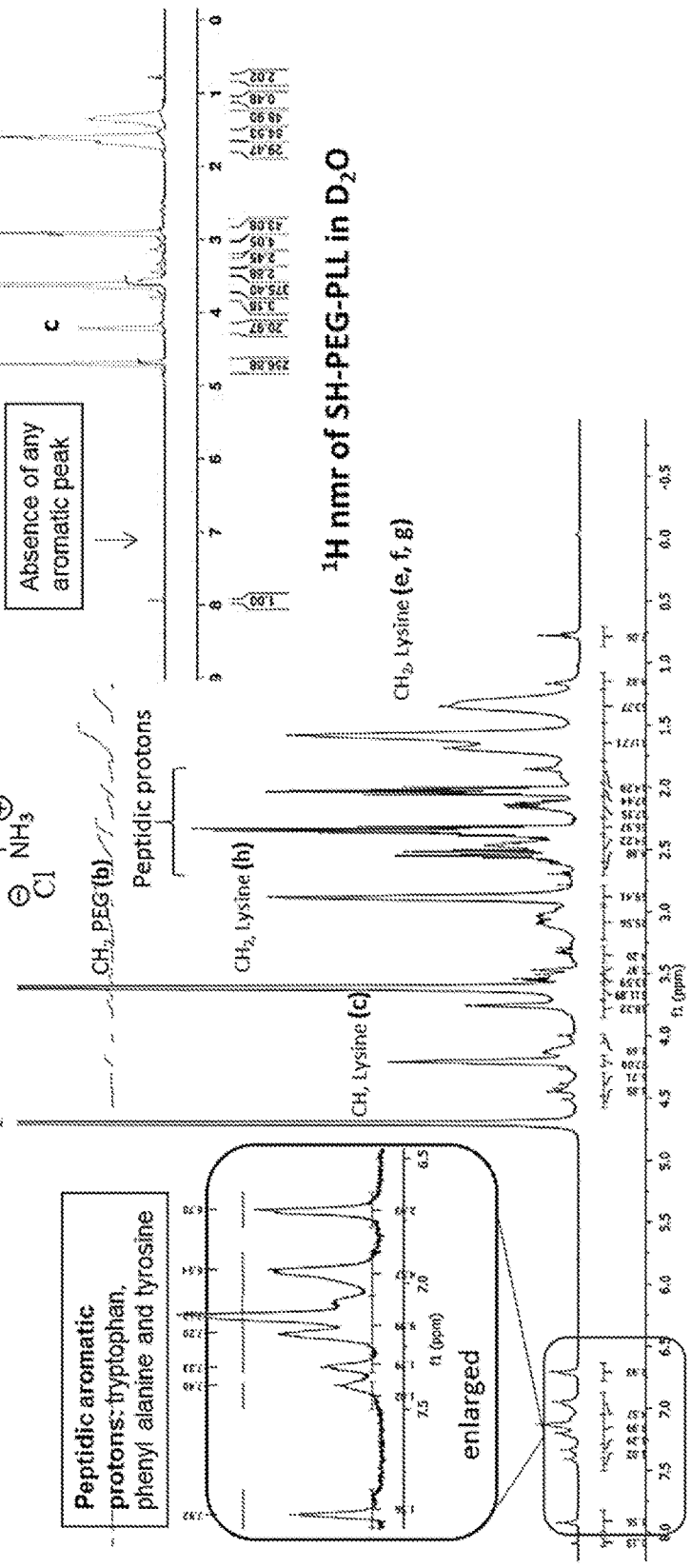
FIG. 12C
Synthesis of Gastrin 10-PEG-PLL block copolymer—$^1$H nmr

SEQUENCE LISTING

<160> NUMBER OF SEQ ID NOS: 4

<210> SEQ ID NO 1
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 1
gugcugagga ugagaacua                                                 19

```
<210> SEQ ID NO 2
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 2
gaugcacccu uagguacag                                                 19

<210> SEQ ID NO 3
<211> LENGTH: 19
<212> TYPE: RNA
<213> ORGANISM: Artificial Sequence
<220> FEATURE:
<223> OTHER INFORMATION: Synthetic oligonucleotide

<400> SEQUENCE: 3
agaagaagcc uauggaugg                                                 19

<210> SEQ ID NO 4
<211> LENGTH: 66
<212> TYPE: DNA
<213> ORGANISM: Artificial Sequence
<220> FEATURE:
<223> OTHER INFORMATION: Synthetic polynucleotide

<400> SEQUENCE: 4
catggtgcag gtgtggctgg gattcatttg ccggtgctgg tgcgtccgcg gccgctaatc    60
ctgttc                                                               66
```

NANOPARTICLE TO TARGET CANCER

This application is the U.S. National Stage of International Application No. PCT/US2017/022567, filed Mar. 15, 2017, which was published in English under PCT Article 21(2), which in turn claims the benefit of U.S. Provisional Appl. No. 62/309,250, filed Mar. 16, 2016, which is incorporated herein by reference in its entirety.

BACKGROUND

Pancreatic ductal adenocarcinoma (PDAC) has a dismal prognosis with the poorest 5-year survival of all gastrointestinal malignancies. Numerous chemotherapeutic agents have been tried to treat unresectable PDAC but none have significantly altered the long term prognosis. There are two principle reasons for this lack of effectiveness. First, most agents used for PDAC are not 'tumor-selective', in that they fail to target PDAC-specific mechanisms or receptors. Second, certain promising treatments, such as RNA interference (RNAi), are broken down in the blood stream; hence, these compounds must be delivered by means that protect from the environment.

SUMMARY

Disclosed herein is a construct, or a pharmaceutically acceptable salt thereof, comprising:
(a) a polyethylene glycol-block-poly(L-lysine) polymer moiety, wherein the polyethylene glycol is thiol-functionalized;
(b) a cholecystokinin-B (CCK-B) receptor ligand coupled to the polyethylene glycol of the polymer moiety; and
(c) a siRNA complexed with the poly(L-lysine) of the polymer moiety,
wherein the construct is neutralized.

Also disclosed herein is a method for making a construct comprising:
(a) conjugating a maleimide-containing gastrin-10 peptide with a block copolymer resulting in a nanoparticle, the block copolymer comprising (i) a thiol-functionalized polyethylene glycol block and (ii) a poly(L-lysine) block; and
(b) mixing the resulting nanoparticle with at least one siRNA.

Additionally disclosed herein is a construct, or a pharmaceutically acceptable salt thereof, comprising:
(a) a polyethylene glycol-block-poly(L-lysine) polymer moiety, wherein the polyethylene glycol is thiol-functionalized;
(b) a cholecystokinin-B (CCK-B) receptor ligand coupled to the polyethylene glycol of the polymer moiety; and
(c) a therapeutically active agent complexed with the poly(L-lysine) of the polymer moiety,
wherein the construct is neutralized.

Further disclosed herein is a method of treating a cancer that possesses a CCK-B receptor, particularly pancreatic cancer, in a subject comprising administering to the subject in need thereof a therapeutically effective amount of any of the constructs or pharmaceutical compositions disclosed herein.

The foregoing will become more apparent from the following detailed description, which proceeds with reference to the accompanying figures.

BRIEF DESCRIPTION OF THE DRAWINGS

FIG. 4A. Pancreatic cancer cells (300,000 per well) were plated into each well of a 12-well tissue culture plate. Cells were treated for 48 hrs with vehicle control, NP bound to scrambled siRNA, or NPs bound to gastrin siRNA at concentrations (120, 240, or 480 nM). Viable cell counts were then perform by trypan exclusion technique. FIGS. 4B-4D. BxPC-3 cancer cells treated for 48 h with Cy3-labeled siRNA NPs show lack of immunofluorescence in PBS controls (FIG. 4B) and increased intracytoplasmic immunofluorescence in cells treated with 240 nM (FIG. 4C) or 480 nM (FIG. 4D) of gastrin siRNA conjugated to NPs. Nuclei shown in blue were reacted with DAPI. FIGS. 4E-4F. Pancreatic cancer cells were treated with NPs carrying gastrin siRNA at 120, 240, or 480 nM, or scrambled siRNA control in NPs or vehicle for 48 hours. RNA was extracted from treated cells and subjected to real-time PCR (qRT-PCR) using SYBR® Green (Life Technologies) and the following gastrin oligonucleotide primers (forward-5'-GCCTCTCATCATCGAAGGCA-3' and Reverse 5'-GCCGAAGTCCATCCATCCAT-3') with GAPDH as the internal control. NPs showed a dose-related decreased in gastrin mRNA. FIGS. 4G-4H. Gastrin peptide immunofluorescence. 150,000 cells were plated onto round coverslips. The following day cells were treated with 120, 240, or 480 nM of gastrin siRNA-polyplex and scramble siRNA-polyplex for 48 hours. The cells were washed, fixed, and incubated with a polyclonal gastrin antibody (Peninsula Labs, Carlsbad, Calif.; 1:1000) overnight at 4° C., followed by incubation with a secondary goat anti-rabbit rhodamine-labeled antibody (Thermo Scientific, Waltham, Mass.; 1:200) for 1 hour at room temperature in the dark. Coverslips were mounted with EverBrite hardset media with DAPI (Biotium, Hayward, Calif.) and imaged by fluorescent microscopy.

FIGS. 6A-6B. FIG. 6A: Non-targeted NPs loaded with ICG show poor tumor uptake. FIG. 6B. Targeted NPs bind to CCK receptors on PDAC tumors in mice and exhibit stable uptake after 7 and 24 hrs.

FIG. 7. Model of polyplex NP between siRNA and gastrin-PEG-b-PLL

FIGS. 12A-12D. Synthesis of the target specific polylysine nanoparticle. FIG. 12A. The thiol functionalized polyethylene glycol-block-poly(L-lysine)(SH-PEG-PLL) polymer was synthesized from trityl-S-PEG-PLL (Tr-S-PEG-PLL) by reducing with trifluoroacetic acid and triethylsilane (98:2 v/v). PEG was conjugated to the polylysine to prolong circulation lifetime and decrease uptake in hematopoietic cells. FIG. 12B. Trityl deprotection was performed and the thiol moiety was purified by proton nuclear magnetic mass spectroscopy. FIG. 12C. Next gastrin-10 was conjugated to the PEG by a maleimide reaction to render the NPs target-specific to the CCK receptor. Maleimide containing targeting peptide, gastrin-10 (3 Maleimido-propionyl-Glu-Glu-Glu-Ala-Tyr-Gly-Trp-Met-Asp-Phe-NH2) was conjugated to the resulting SH-PEG-PLL via Michael addition reaction at pH 7 in deoxygenated HEPES buffer (100 mM) under an inert atmosphere. After conjugation, the gastrin-10 peptide containing polymer (Ga-PEG-PLL) was extensively purified using a PD-10 column (size exclusion chromatography) and further by dialysis (membrane cut-off 6-8 KD MW) against PBS for 48 hours. FIG. 12D. Finally, the polyplex micelle was prepared by mixing 1mg/mL of the Ga-PEG-b-PLL with various N/P ratios of gastrin siRNA (si286 GUGCUGAG-GAUGAGAACUA) in 20 mM HEPES buffered saline (HBS pH 7.4), followed by 30 min incubation at room temperature to allow polyplex formation.

FIG. 13A. Nanoparticles that were either targeted to the CCK-B receptor or untargeted were loaded with Cy3 labeled gastrin siRNA. Mice bearing BxPC-3 orthotopic pancreatic cancer were then injected intraperitoneally with the NPs and imaged by fluorescent microscopy. Only the mice receiving the targeted NPs showed fluorescent uptake within the tumors. There was no uptake of fluorescent particles detected in the mice treated with untargeted NPs. FIG. 13B. Tumor size was determined using software on an IVIS imaging system (Xenogen Corp, Alameda, Calif.). Graph of estimated average flux by IVIS imaging of mice in each treatment group bearing BxPC-3 tumors. All tumor fluxes were equal before initiation of therapy and one week after tumor inoculation. Although the targeted NP-treated mice with BxPC-3 tumors had less flux, this was not significant due to variability in groups. FIG. 13C. Ten minutes prior to imaging, luciferin (Nanolight Technology) was administered to mice (using a 27.5 g needle i.p.) at a concentration of 135 mg/kg in a volume of 100 µl. IVIS imaging of a representative mouse from each group showing smaller PANC-1 tumor volume size in the mice treated with targeted gastrin siRNA only. FIG. 13D. Regression analysis of mean flux values over time in each treatment group of mice bearing PANC-1 tumors. FIG. 13E. The final tumor weights were measured at the termination of the experiment and only the mice treated with targeted gastrin siRNA NPs had significantly smaller tumor masses without any metastases. FIG. 13F. No metastases were found in either the mice bearing either BXPC-3 or PANC-1 tumors. However, metastases were frequent in the untargeted and control NP-treatment groups. A representative Hematoxylin & eosin histologic section of a liver metastasis is show from the control untargeted scrambled NP-treated group.

SEQUENCE LISTING

Figure 1:
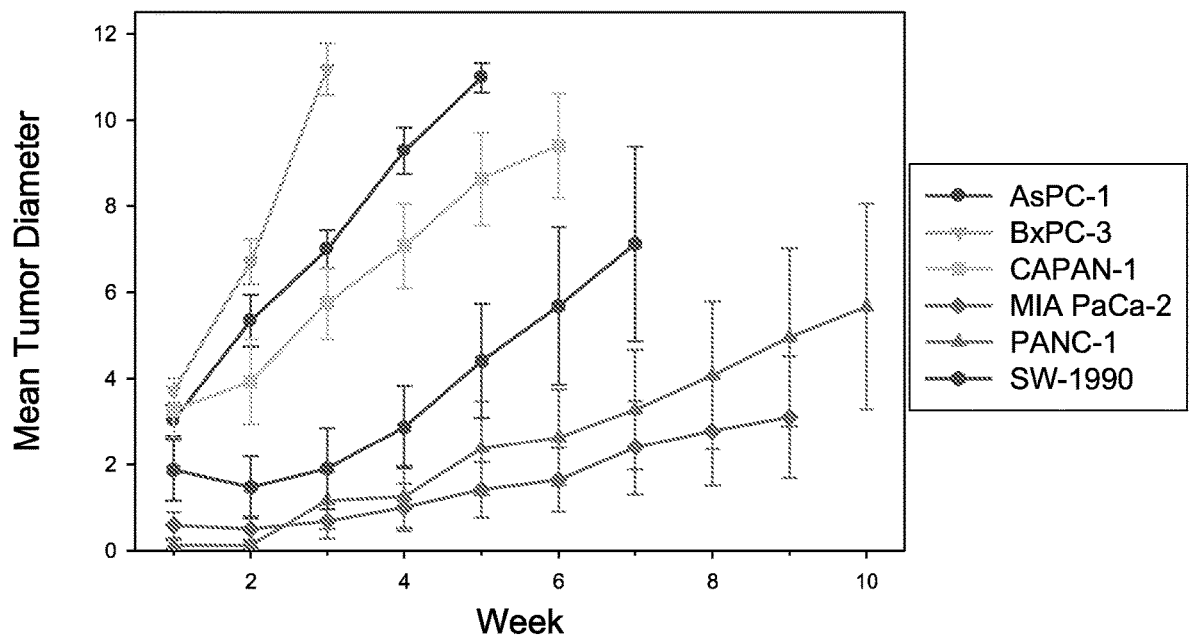
FIG. 1. Pancreatic tumor growth rates directly parallel the amount of gastrin mRNA expressed. BxPC-3 & AsPC-1 grow the fastest and produce the highest level of gastrin.

The nucleic acid sequences listed in the accompanying sequence listing are shown using standard letter abbreviations for nucleotide bases as defined in 37 C.F.R. 1.822. Only one strand of each nucleic acid sequence is shown, but the complementary strand is understood as included by any reference to the displayed strand. The Sequence Listing is submitted as an ASCII text file, created on Mar. 14, 2017, 1.18 KB, which is incorporated by reference herein.

DETAILED DESCRIPTION

Terminology

The following explanations of terms and methods are provided to better describe the present compounds, compositions and methods, and to guide those of ordinary skill in the art in the practice of the present disclosure. It is also to be understood that the terminology used in the disclosure is for the purpose of describing particular embodiments and examples only and is not intended to be limiting.

"Administration" as used herein is inclusive of administration by another person to the subject or self-administration by the subject.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Inhibiting" refers to inhibiting the full development of a disease or condition. "Inhibiting" also refers to any quantitative or qualitative reduction in biological activity or binding, relative to a control.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

A "therapeutically effective amount" refers to a quantity of a specified agent sufficient to achieve a desired effect in a subject being treated with that agent. Ideally, a therapeutically effective amount of an agent is an amount sufficient to inhibit or treat the disease or condition without causing a substantial cytotoxic effect in the subject. The therapeutically effective amount of an agent will be dependent on the subject being treated, the severity of the affliction, and the manner of administration of the therapeutic composition.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. The phrase "treating a disease" refers to inhibiting the full development of a disease, for example, in a subject who is at risk for a disease such as diabetes. "Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's *Pharmaceutical Sciences*, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid, phosphoric acid, methanesulfonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. "Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. These salts may be prepared by standard procedures, for example by reacting the free acid with a suitable organic or inorganic base. Any chemical compound recited in this specification may alternatively be administered as a pharmaceutically acceptable salt thereof. "Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., *J. Pharm. Sci.* 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_i$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound.

The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term "addition salt" as used hereinabove also comprises the solvates which the compounds described herein are able to form. Such solvates are for example hydrates, alcoholates and the like.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

Overview

A membrane bound growth receptor called the cholecystokinin or CCK-receptor has been identified that is overexpressed in human pancreatic cancer cells. Pancreatic ductal adenocarcinoma (PDAC) markedly over-expresses the cholecystokinin-B (CCK-B) receptor and re-expression of gastrin that stimulates growth of PDAC by an autocrine mechanism through the CCK-B receptor. When gastrin mRNA is down regulated by RNAi techniques, PDAC growth and metastases are inhibited in animal models. However, anti-gastrin gene therapy cannot be readily used in humans unless nontoxic gene delivery strategies are implemented.

Over 90% of human pancreatic cancers have mutated KRAS that is thought to be a driver of this malignancy. If KRAS is turned off or downregulated, carcinogenesis is arrested. Researchers have been trying to develop strategies to eliminate or block KRAS as a means to inhibit PDAC growth. However, as with other gene therapies, delivery vehicles that safely bind to the cancer without off target toxicity have yet to be developed.

Although RNA interference is a biological process and an effective tool that is useful in studying gene expression in vitro, translating its use clinically has been challenging. Various carrier vehicles to transport silencing RNA (siRNA) to tissues in vivo have been utilized; however, safe and effective delivery remains problematic. Here we report the development of a polyplex nanoparticle (NP) that selectively targets the cholecystokinin receptor on human pancreatic cancer and delivers specific siRNA to the peptide gastrin to block cancer cell growth in vitro and in vivo. The nanoparticle was developed on a polyethylene glycol(PEG)-block-poly(L-Lysine) backbone and a stable thioether link was used to conjugate the ligand to the PEG rendering it receptor specific. Cellular uptake of NP showed fluorescently-labeled siRNA was localized to the cellular lysosome by confocal microscopy. Receptor targeted gastrin siRNA NP treatment of pancreatic cancer cells and tumors in mice inhibited growth, decreased gastrin expression, and inhibited metastases compared to vehicle-PBS, untargeted siRNA, targeted scrambled RNA controls. These findings show effective target-specific delivery of siRNA to inhibit growth of pancreatic cancer.

Exploiting this pancreatic cancer-specific target, disclosed herein are block copolymer (polyethylene glycol-block-polylysine (PEG-b-PLL) nanoparticles (polyplex NPs) that bind selectively to the CCK-receptor and deliver a payload of small interfering RNAs (siRNA) to pancreatic cancer. In particular, the nanoparticles are linked to CCK receptor ligand (e.g., gastrin-10 peptide or a DNA aptamer) to the poly-L-lysine (PLL) of the nanoparticle through a short PEG segment using maleimide chemistry. With regard to gene therapy, two target genes have been shown to drive pancreatic cancer growth: GASTRIN and mutated KRAS. GASTRIN- and mutant KRAS-targeted siRNA are added to the block copolymer construct by electrostatic complexation. These form a micelle that is biodegradable and nontoxic that inhibits growth of pancreatic cancer.

The constructs and methods disclosed herein can target other cancer associated receptors to provide cancer specific treatments and the gene of interest can be designed to knockdown and decrease expression of any cancer protein that is linked to growth or metastases. Other illustrative cancers that express CCK receptors include stomach, colon, brain, lung cancer and some thyroid cancers.

Other therapeutically active agents can be complexed with the poly(L-lysine) of the constructs disclosed herein. For example, siRNA to collagen peptides (such as matrix metalloproteases, SMA-α, fibronectin, laminin, integrin); cell adhesion molecules such as cadherin-like proteins; intracellular signaling proteins associated with cancer (such as (TGF-β FGF, EGF, HGF, Wnt/beta-catenin and Notch); KRAS downstream effectors (such as canonical Raf/Mek/Erk, phosphatidylinositol 3-kinase (PI3K)/3-phosphoinositide-dependent protein kinase-1 (Pdk1)/Akt, JAX/STAT, Ral-GDS/p38MAPK, Rac and Rho, Rassf1, NF1, p120GAP and PLC-ε); and endothelial pathways activated in cancer (such as VEGF-A) could be complexed with the poly(L-lysine) for delivery to the pancreas for treating pancreatic cancer. Since CCK-B receptors are also present on a variety of other cancers such as colorectal cancer, gastric cancer, distal esophageal adenocarcinoma, medullary thyroid cancer, small cell lung cancer (SCLC), and carcinoid tumors, the poly-lysine NP disclosed herein can target gene expression through the CCKB receptor in numerous cancers. Other therapeutically active agents may be RNA based therapeutics such as microRNAs (miRNAs) antisense oligonucleotides (ASOs), aptamers, synthetic messenger RNA (mRNAs), or any therapeutically active agents (i.e., chemotherapeutics or biologics) covalently conjugated to polyanions such as poly(aspartic acid), poly(glutamic acid), poly(carboxyl ε-caprolactone), heparin or carboxymethylated dextran.

CCK and Gastrin Stimulate Growth of Pancreatic Cancer:

The natural physiologic ligands for the CCK-R include the related gastrointestinal peptides gastrin and CCK. In the adult, gastrin is the major mediator of gastric acid secretion and gastrointestinal growth and is locally synthesized in the G-cells of the stomach antrum. CCK is structurally related to gastrin and acts physiologically on CCK receptors to regulate secretion of digestive enzymes and growth of the pancreas. CCK is responsible for regeneration after insult to the pancreas, such as after a bout of pancreatitis. It addition to being important growth factors to the pancreas, it has become apparent that these peptides also stimulates growth of pancreatic cancer through the CCK receptor. In addition to responding to the exogenous application of gastrin, PDAC also produces its own gastrin (not CCK) and stimulates growth through an autocrine mechanism. Gastrin is not found in the normal adult pancreas and its expression or re-expression is found in PanINs and in cancer of the pancreas. The growth rate of PDAC in nude mice is directly proportional to the amount of gastrin mRNA the tumor produces. If gastrin expression is down-regulated, pancreas cancer cells and tumors fail to grow or metastasize.

Gastrin Regulates Pancreatic Cancer by an Autocrine Mechanism:

Embryologically gastrin is present in the developing human and murine pancreas, but levels rapidly decrease to zero after birth, and there is no gastrin peptide found in the adult pancreas. Confirmation that the role of gastrin expression is related to proliferation is supported by evidence that growth is significantly impaired when gastrin is down regulated in pancreatic cancer cells in vitro. The autocrine mechanism of gastrin is substantiated by the finding that endogenous gastrin from cancer can induce its own transcription by activating the CCK-receptor. Thus, pancreatic cells that produce gastrin embryologically become 'silenced' in the normal adult pancreas until something changes to reactivate its expression. Although both gastrin and CCK stimulate growth of pancreatic cancer through the CCK receptor, prior studies have shown that only gastrin stimulates growth by the autocrine mechanism. Also, studies have shown that although murine models typically express the CCK-A variety of receptor in normal cells, the CCK-B receptor phenotype is expressed in both human and murine cancer. In human PDAC cell such as PANC-1 cells that express both CCK-A and CCK-B receptors, only antagonists to the CCK-B receptor block the stimulatory effects of both gastrin and/or CCK supporting the evidence that growth is mediated through the CCK-B receptor phenotype.

CCK receptors are G-protein coupled receptors that bind the ligands CCK and gastrin. Normal pancreas tissues, pancreatic cancer cell lines from culture, and fresh cancer specimens from the operating room were characterized by radioactive CCK receptor binding kinetic assays, and it was found that the CCK receptor is markedly over-expressed in all pancreatic cancers compared to normal tissues, with high binding affinities (nM range) to its ligand and/or antagonist (Table 1).

TABLE 1

Receptor binding assays show the marked increased expression of CCK receptors on pancreatic cancer cells and tumors. The Kd is in the physiologic nanomolar range.

| Tissue/Cell Line | Binding Affinity Kd, (nM) | Receptor number Bmax (fmol/mg protein) |
|---|---|---|
| PANC-1 cells | 4.3 ± 0.6 | 283 ± 68 |
| MDA-Panc-28 | 3.6 ± 0.1 | 273 ± 22 |
| MDA-Amp-7 | 2.0 ± 0.4 | 211 ± 54 |
| MIA PaCa-2 | 3.0 ± 0.7 | 151 ± 12 |
| Capan-1 | 2.7 ± 1.3 | 149 ± 83 |
| BxPC-3 | 3.4 ± 0.1 | 125 ± 44 |
| Fresh cancer from surgery | 2.3 ± 0.8 | 285 ± 36 |
| Normal pancreas | 1.8 ± 0.7 | 68 ± 7.2 |

Figure 2:
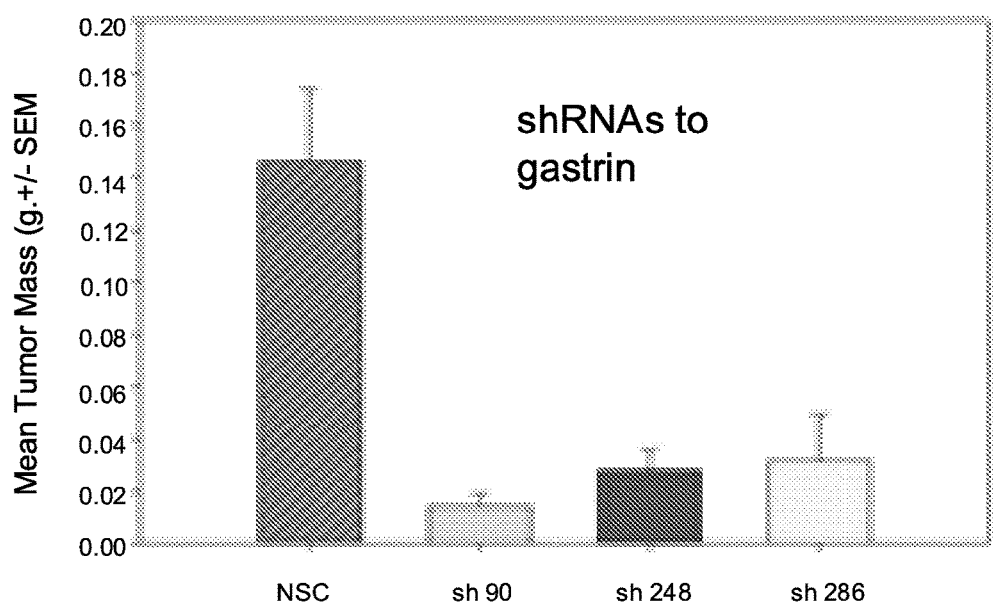
FIG. 2. BxPC-3 orthotopic tumor growth is significantly reduced ($p<0.002$) by down-regulation of gastrin expression through shRNA transfection FIG. 3. Pancreatic cancer cells are treated with either siRNA for mutated Kras (left), scrambled siRNA control, diluents, or untreated and amount of gene measured by qRT-PCR show inhibition of Kras FIGS. 4A-4H. Effects of gastrin siRNA NPs on growth of pancreatic cancer in vitro.
Figure 3:
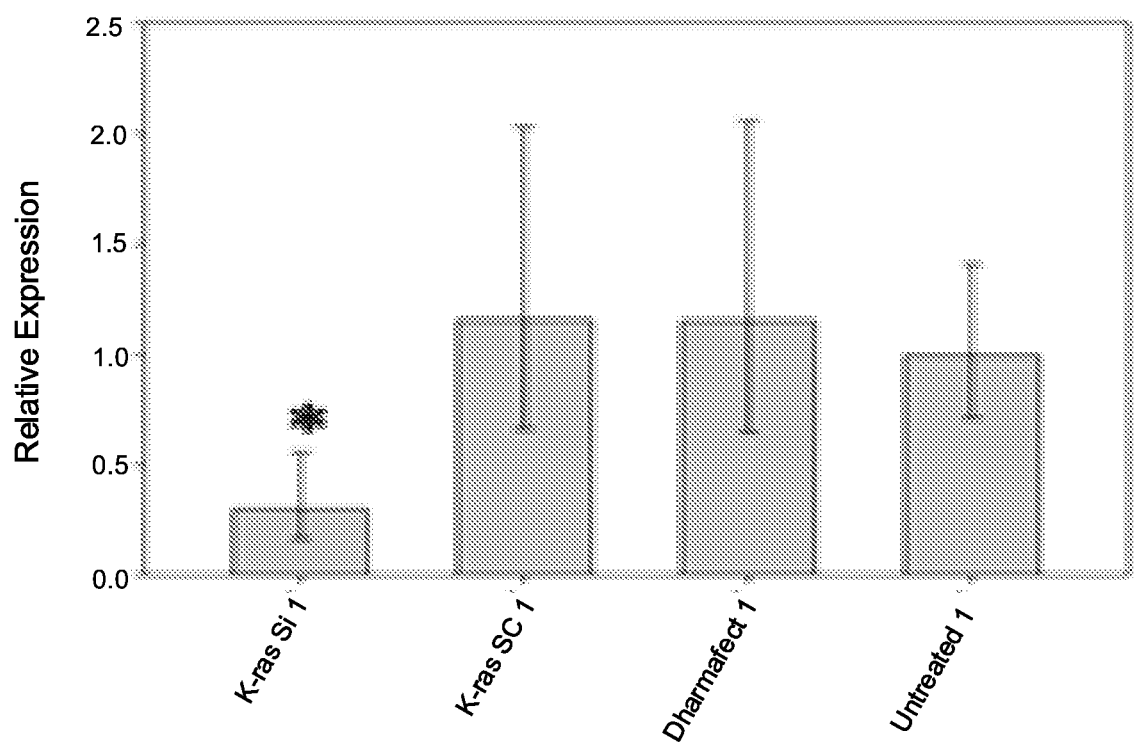

Gene Therapy for Pancreatic Cancer:

One aspect of the technology disclosed herein is to attack PDAC with gene therapy using siRNA technology known to impair growth of this cancer. For example, the constructs and methods disclosed herein enable the down regulation of the two driver genes, GASTRIN and mutated KRAS, due to their ubiquity in PDAC and role in proliferation. Gastrin is not detected in the normal pancreas but becomes re-expressed in PanIN lesions and cancer where it stimulates growth of PDAC by an autocrine mechanism. Cancer growth rate is directly proportional to the concentration of gastrin mRNA in the pancreatic cancer cells (FIG. 1) and all pancreatic cancer cells and tissues tested to date, express endogenous gastrin. Treatment of pancreatic cancer cells in vitro with antisense oligonucleotides to gastrin decreases cell proliferation, and down-regulation of gastrin by siRNAs inhibits PDAC growth and metastases in vivo (FIG. 2) confirming that gastrin mRNA is a good target for cancer therapy. Mutations of KRAS are found in about 90% of PDAC and this mutation has been utilized to develop a transgenic mouse model of pancreatic carcinogenesis. We have also shown that we can selectively decrease mutated Kras in AsPC-1 human pancreatic cancer cells by siRNA techniques (FIG. 3).

Figure 5:
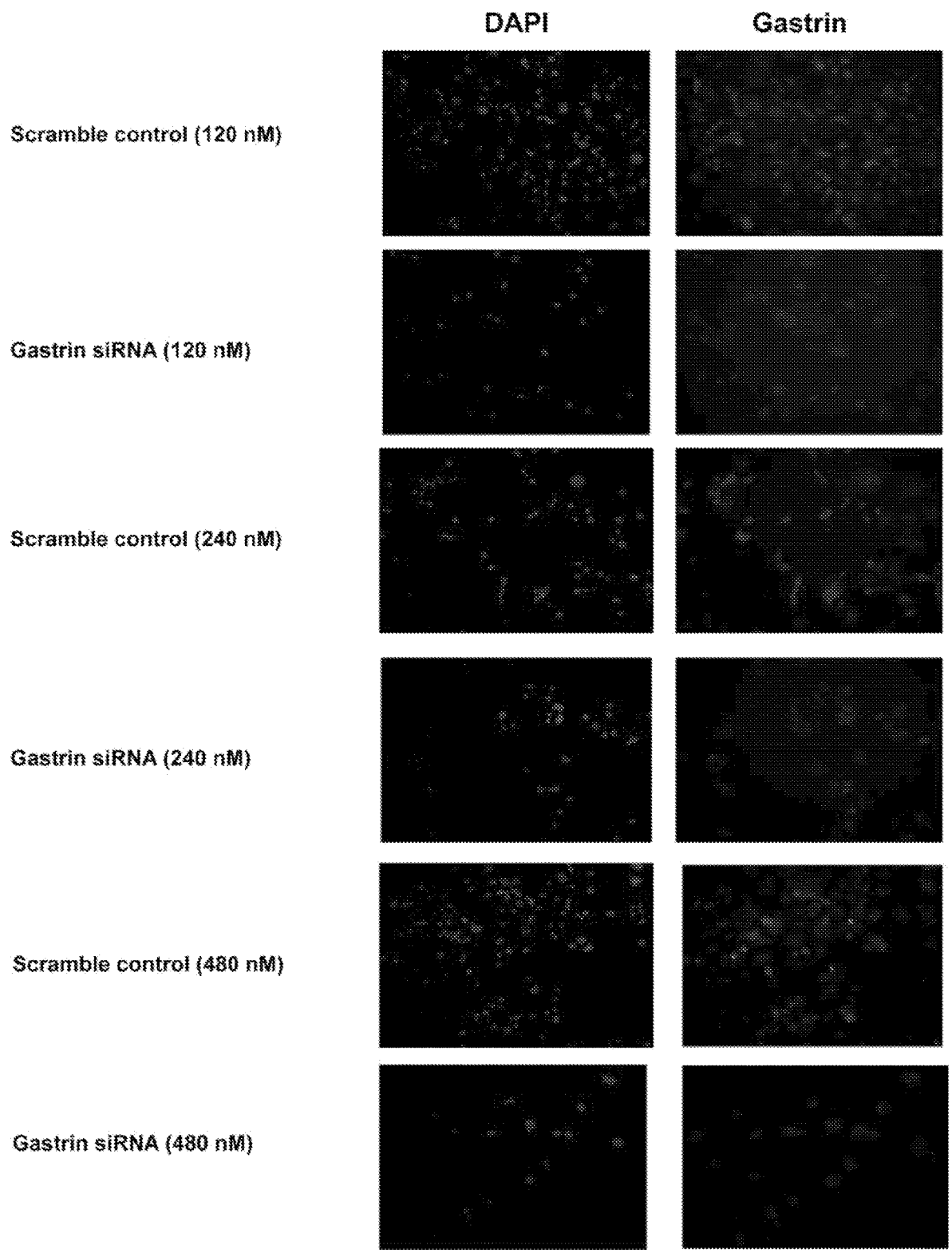
FIG. 5. Gastrin immunofluorescence. Pancreatic cancer cells were treated with polyplex gastrin siRNA NPs or scrambled controlled NPs at 3 concentrations×48 h. The cells were then fixed on the glass coverslips and reacted with a gastrin peptide rabbit polyclonal antibody followed by a secondary anti-rabbit rhodamine antibody. Nuclei were stained with DAPI. The figure shows that gastrin peptide expression is significantly decreased in the cells treated with the gastrin siRNA NPs but not the gastrin scrambled control RNAi in NPs.

Use of Nanotechnology for siRNA Delivery to Tumors:

We performed gastrin siRNA transfection studies with polyplex NPs and demonstrated uptake of the nanoliposomes laden with Cy3-fluorescently labeled gastrin siRNA into pancreatic cancer cells (FIGS. 4A-4H). In FIG. 5 we have shown that gastrin siRNA laden polyplex nanoparticles successfully decreased gastrin immunoreactivity in human pancreatic cancer cells, indicating that the siRNA was active after uptake and capable of decreasing gastrin peptide.

Development of a Novel Polyplex Nanoparticle (NP) for Pancreatic Cancer:

Disclosed herein are novel NPs to deliver siRNA using a CCK-receptor-targeted polyethylene glycol-block-poly(L-lysine) (PEG-b-PLL) polyplex. The targeted PEG-b-PLL polyplexes was designed to contain three basic features: (i) a short cationic segment (PLL) for the complexation of siRNA, (ii) a hydrophilic and biologically inert segment (PEG), and (iii) a cell surface targeting moiety (a peptide, gastrin-10). This block copolymer design will facilitate small polyplex formation following electrostatic interaction between the cationic polylysine moiety and negatively charged siRNA, resulting in charge neutralization and self-assembly into a polyplex structure with siRNA contained in the core surrounded by PEG conjugated to the targeting ligand gastrin-10 on the surface (FIG. 7). In certain embodiments, the polyplex disclosed herein is in the form of a micelle. The conjugation of gastrin-10 to the PEG-b-PLL polymer is performed via maleimide-thiol coupling chemistry.

In particular, the block copolymer includes two block moieties: (1) thiol-functionalized polyethylene glycol (PEG); and (2) poly(L-lysine) (PLL). The block copolymer (referred to herein as "SH-PEG-PLL") may have a structure represented by

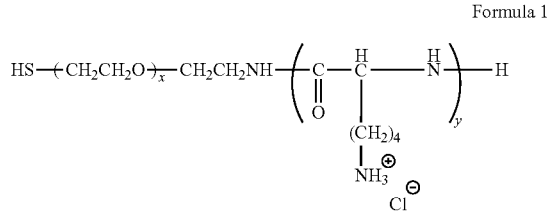

Formula 1 wherein x is 22 to 454, more particularly 45 to 275; and y is 10 to 100, more particularly 20 to 50. The number-average molecular weight of the PEG may range from 1000 Da to 20,000 Da. The number-average molecular weight of the PLL may range from 1600 Da to 16000 Da. In certain embodiments, x is 113 and y is 27, and the PEG molecular weight is 5000 g/mole (Da) and the PLL molecular weight is 4400 Da. In certain embodiments, 10 to 30%, more particularly about 20% of the PEG chains are thiol functionalized.

The maleimide-containing gastrin-10 peptide may have a structure of:
3-maleimido-propionyl-Glu-Glu-Glu-Ala-Tyr-Gly-Trp-Met-Asp-Phe-NH$_2$
(molecular formula: C65H79N13O22S; molecular weight: 1426.48 Da).
The maleimide-containing gastrin-10 peptide can be conjugated to any thiol (—SH) group through Michael addition to form a stable thioether bond.

The resulting nanoparticle has a structure of:

Formula 2

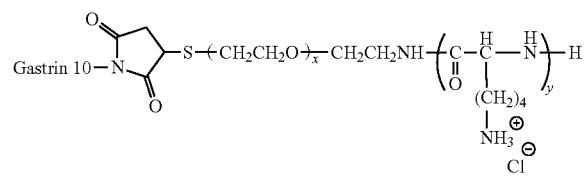

wherein x and y are the same as above.

In certain embodiments, the nanoparticle construct together has a structure of:

Formula 3

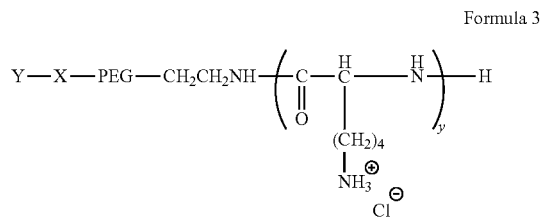

wherein Y is the cholecystokinin-B (CCK-B) receptor ligand; X is a linker; PEG is polyethylene glycol; and y is 10 to 200, more particularly 20 to 50.

The linker X may be a thioether or a group derived from a methoxy or carboxy linking agent.

At least one siRNA is mixed with the nanoparticle under conditions sufficient for electrostatically complexing the siRNA with the poly(L-lysine) of the polymer moiety. For example, GASTRIN-targeted siRNA and/or mutant KRAS-targeted siRNA may be added to the block copolymer construct by electrostatic complexation. The relative concentrations of the nanoparticle and the siRNA may vary. In certain embodiments, the relative concentrations are appropriate to provide N/P (nitrogen of polylysine amine (NH$_2^+$) verses phosphate (PO$_4^-$) of siRNA) of 0.5 to 20, more particularly 2 to 10.

In certain embodiments, the siRNA may be gastrin siRNA (si286 GUGCUGAGGAUGAGAACUA (SEQ ID NO: 1), GAUGCACCCUUAGGUACAG (SEQ ID NO: 2) or AGAAGAAGCCUAUGGAUGG (SEQ ID NO: 3).

The cholecystokinin-B (CCK-B) receptor ligand may be gastrin-10 or a DNA aptamer as disclosed, for example, in Nucleic Acid Ther. 2017 Feb. 1; 27(1):23-35). An illustrative DNA aptamer has a structure of:

(SEQ. ID No: 4)
CATGGTGCAG GTGTGGCTGG GATTCATTTG CCGGTGCTGG
TGCGTCCGCG GCCGCTAATC CTGTTC.

Disclosed herein are NPs labeled with ligand to the CCK receptor that demonstrated specific uptake and internalization into orthotopic PDAC tumors in mice.

The nanoparticles disclosed herein are biodegradable and biocompatible. Furthermore, when assembled, the nanoparticles will protect the siRNA from degradation in the NP core.

The NP can deliver anti-gastrin gene therapy in the form of siRNA into human pancreatic cancer cells to significantly inhibit cell growth by downregulation of gastrin expression. This technique may provide a safe and novel gene therapy delivery method to treat those with advanced PDAC.

Pharmaceutical Compositions and Methods of Use

In some embodiments, the methods disclosed herein involve administering to a subject in need of treatment a pharmaceutical composition, for example a composition that includes a pharmaceutically acceptable carrier and a therapeutically effective amount of one or more of the constructs disclosed herein. The constructs may be administered parenterally (including subcutaneous injections (SC or depo-SC), intravenous (IV), intramuscular (IM or depo-IM), intrasternal injection or infusion techniques), sublingually, intranasally (inhalation), intrathecally, topically, ophthalmically, or rectally. The pharmaceutical composition may be administered in dosage unit formulations containing conventional non-toxic pharmaceutically acceptable carriers, adjuvants, and/or vehicles. The constructs are preferably formulated into suitable pharmaceutical preparations such as tablets, capsules, or elixirs for oral administration or in sterile solutions or suspensions for parenteral administration. Typically the constructs described above are formulated into pharmaceutical compositions using techniques and procedures well known in the art.

For example, the pharmaceutical compositions may be in a dosage unit form such as an injectable fluid, a nasal delivery fluid (e.g., for delivery as an aerosol or vapor), a semisolid form (e.g., a topical cream), or a solid form such as powder, pill, tablet, or capsule forms.

In some embodiments, one or more of the disclosed constructs (including compounds linked to a detectable label or cargo moiety) are mixed or combined with a suitable pharmaceutically acceptable carrier to prepare a pharmaceutical composition. Pharmaceutical carriers or vehicles suitable for administration of the constructs provided herein include any such carriers known to be suitable for the particular mode of administration. *Remington: The Science and Practice of Pharmacy*, The University of the Sciences in Philadelphia, Editor, Lippincott, Williams, & Wilkins, Philadelphia, Pa., 21$^{st}$ Edition (2005), describes exemplary compositions and formulations suitable for pharmaceutical delivery of the compounds disclosed herein. In addition, the constructs may be formulated as the sole pharmaceutically active ingredient in the composition or may be combined with other active ingredients.

Upon mixing or addition of the construct(s) to a pharmaceutically acceptable carrier, the resulting mixture may be a solution, suspension, emulsion, or the like. These may be prepared according to methods known to those skilled in the art. The form of the resulting mixture depends upon a number of factors, including the intended mode of administration and the solubility of the construct in the selected carrier or vehicle. Where the constructs exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the constructs, such as salts or prodrugs may also be used in formulating effective pharmaceutical compositions. The disclosed constructs may also be prepared with carriers that protect them against rapid elimination from the body, such as time-release formulations or coatings. Such carriers include controlled release formulations, such as, but not limited to, microencapsulated delivery systems.

The disclosed constructs and/or compositions can be enclosed in multiple or single dose containers. The constructs and/or compositions can also be provided in kits, for example, including component parts that can be assembled for use. For example, one or more of the disclosed constructs may be provided in a lyophilized form and a suitable diluent may be provided as separated components for combination prior to use. In some examples, a kit may include a disclosed construct and a second therapeutic agent (such as an anti-retroviral agent) for co-administration. The construct and second therapeutic agent may be provided as separate component parts. A kit may include a plurality of containers, each container holding one or more unit dose of the construct. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The active construct is included in the pharmaceutically acceptable carrier in an amount sufficient to exert a therapeutically useful effect in the absence of undesirable side effects on the subject treated. A therapeutically effective concentration may be determined empirically by testing the constructs in known in vitro and in vivo model systems for the treated disorder. In some examples, a therapeutically effective amount of the construct is an amount that lessens or ameliorates at least one symptom of the disorder for which the compound is administered. Typically, the compositions are formulated for single dosage administration. The concentration of active construct in the drug composition will depend on absorption, inactivation, and excretion rates of the active construct, the dosage schedule, and amount administered as well as other factors known to those of skill in the art.

In some examples, about 0.1 mg to 1000 mg of a disclosed construct, a mixture of such construct, or a physiologically acceptable salt or ester thereof, is compounded with a physiologically acceptable vehicle, carrier, excipient, binder, preservative, stabilizer, flavor, etc., in a unit dosage form. The amount of active substance in those compositions or preparations is such that a suitable dosage in the range indicated is obtained. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient. In some examples, the compositions are formulated in a unit dosage form, each dosage containing from about 1 mg to about 1000 mg (for example, about 2 mg to about 500 mg, about 5 mg to 50 mg, about 10 mg to 100 mg, or about 25 mg to 75 mg) of the one or more constructs. In other examples, the unit dosage form includes about 0.1 mg, about 1 mg, about 5 mg, about 10 mg, about 20 mg, about 30 mg, about 40 mg, about 50 mg, about 60 mg, about 70 mg, about 80 mg, about 90 mg, about 100 mg, about 150 mg, about 200 mg, about 250 mg, about 300 mg, about 400 mg, about 500 mg, about 600 mg, about 700 mg, about 800 mg, about 900 mg, about 1000 mg, or more of the disclosed construct(s).

The disclosed constructs or compositions may be administered as a single dose, or may be divided into a number of smaller doses to be administered at intervals of time. The therapeutic compositions can be administered in a single dose delivery, by continuous delivery over an extended time period, in a repeated administration protocol (for example, by a multi-daily, daily, weekly, or monthly repeated administration protocol). It is understood that the precise dosage, timing, and duration of treatment is a function of the disease being treated and may be determined empirically using known testing protocols or by extrapolation from in vivo or in vitro test data. It is to be noted that concentrations and dosage values may also vary with the severity of the condition to be alleviated. In addition, it is understood that for a specific subject, dosage regimens may be adjusted over time according to the individual need and the professional judgment of the person administering or supervising the administration of the compositions, and that the concentration ranges set forth herein are exemplary only.

Injectable solutions or suspensions may also be formulated, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid. Solutions or suspensions used for parenteral, intradermal, or subcutaneous application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers.

The constructs can be administered parenterally, for example, by IV, IM, depo-IM, SC, or depo-SC. When administered parenterally, a therapeutically effective amount of about 0.1 to about 500 mg/day (such as about 1 mg/day to about 100 mg/day, or about 5 mg/day to about 50 mg/day) may be delivered. When a depot formulation is used for injection once a month or once every two weeks, the dose may be about 0.1 mg/day to about 100 mg/day, or a monthly dose of from about 3 mg to about 3000 mg.

The constructs can also be administered sublingually. When given sublingually, the constructs should be given one to four times daily in the amounts described above for IM administration.

The constructs can also be administered intranasally. When given by this route, the appropriate dosage forms are a nasal spray or dry powder. The dosage of the constructs for intranasal administration is the amount described above for IM administration. When administered by nasal aerosol or inhalation, these compositions may be prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents.

The constructs can be administered intrathecally. When given by this route, the appropriate dosage form can be a parenteral dosage form. The dosage of the compounds for intrathecal administration is the amount described above for IM administration.

It should be apparent to one skilled in the art that the exact dosage and frequency of administration will depend on the particular constructs administered, the particular condition being treated, the severity of the condition being treated, the age, weight, general physical condition of the particular subject, and other medication the individual may be taking as is well known to administering physicians.

Several embodiments are described below in consecutively numbered clauses:

1. A construct, or a pharmaceutically acceptable salt thereof, comprising:

(a) a polyethylene glycol-block-poly(L-lysine) polymer moiety, wherein the polyethylene glycol is thiol-functionalized;

(b) a cholecystokinin-B (CCK-B) receptor ligand coupled to the polyethylene glycol of the polymer moiety; and (c) a siRNA complexed with the poly(L-lysine) of the polymer moiety, wherein the construct is neutralized.

2. The construct of clause 1, wherein the construct is a nanoparticle having an average hydrodynamic size (Z Ave 48 nm) of less than 100 nm.

3. The construct of clause 1, wherein the construct is a nanoparticle having an average hydrodynamic size (Z Ave 48 nm) of 30 to 60 nm.

4. The construct of any one of clauses 1 to 3, wherein the siRNA is a GASTRIN-targeted siRNA, a mutant KRAS-targeted siRNA, or a combination thereof.

5. The construct of any one of clauses 1 to 4, wherein the cholecystokinin-B (CCK-B) receptor ligand comprises gastrin-10.

6. The construct of any one of clauses 1 to 5, wherein the cholecystokinin-B (CCK-B) receptor ligand has a structure of 3-maleimido-propionyl-Glu-Glu-Glu-Ala-Tyr-Gly-Trp-Met-Asp-Phe-NH$_2$.

7. The construct of any one of clauses 1 to 6, wherein the (a) and (b) moieties of the construct together have a structure of:

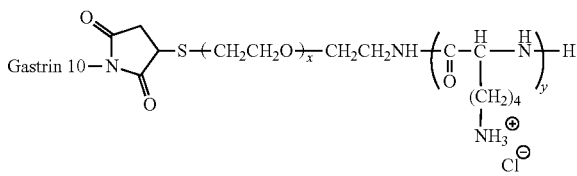

wherein x is 22 to 454, more particularly 45 to 275; and y is 10 to 200, more particularly 20 to 50.

8. A pharmaceutical composition comprising at least one pharmaceutically acceptable addition and at least one construct of any one of clauses 1 to 7.

9. A method for making a construct comprising:

(a) conjugating a maleimide-containing gastrin-10 peptide with a block copolymer resulting in a nanoparticle, the block copolymer comprising (i) a thiol-functionalized polyethylene glycol block and (ii) a poly(L-lysine) block; and (b) mixing the resulting nanoparticle with at least one siRNA.

10. A method of treating pancreatic cancer in a subject comprising administering to the subject in need thereof a therapeutically effective amount of the construct of any one of clauses 1 to 7.

Examples

In order to develop the targeted NP, a thiol functionalized polyethylene glycol-block-poly(L-lysine) (SH-PEG-PLL) polymer was synthesized. To render the NP target-specific for the CCK-B receptor a maleimide link was used to conjugate Gastrin-10 to the PEG via Michael addition reaction. In other embodiments, the nanoparticle can be made target specific to the CCK-B receptor by using a maleimide link to conjugate a DNA aptamer to the PEG. The resulting Ga-PEG-PLL was extensively purified using a PD-10 column and by dialysis. The polyplex micelle was prepared by mixing 1mg/mL of the Ga-PEG-b-PLL with a gastrin siRNA (si286 GUGCUGAGGAUGAGAACUA (SEQ ID NO: 1)), which decreases gastrin mRNA 90%. The PEG protects the siRNA from degradation in solution or blood and the lysine polymer forms a micelle shielding the positive charge and eliminating toxicity. Other siRNA that could be used include GAUGCACCCUUAGGUACAG (SEQ ID NO: 2) and AGAAGAAGCCUAUGGAUGG (SEQ ID NO: 3). The NP was analyzed by dynamic light scattering (DLS) and zeta potential. Efficacy of the NPs to inhibit growth was tested on PANC-1 human PDAC cells that have a high number of CCK-B receptors. Cells were plated into 6-well plates overnight and then treated ×72 h with PBS, 100×NP (10 nM siRNA) or 50×NPs (5 nM siRNA) in serum-free DMEM media. Viable cell counts were performed by trypan blue exclusion.

Characterization of the functionalized polyplex NP confirmed a molecular weight of 9700 Da. Trityl deprotection and conjugation of Ga-10 to the SH-PEG-PLL polymer were confirmed by NMR which demonstrated complete removal of the trityl group and greater than 70% conjugation of the peptide to target the receptor. The polyplex NP complex was confirmed by DLS measurement, which demonstrated size distributions of 44.3±0.3 and 48.2±0.3 nm for receptor-targeted and untargeted polyplex respectively. Treatment of PANC-1 cancer cells with the anti-gastrin NPs significantly inhibited growth by 98% compared to untreated controls (p=0.005).

Methods for Design of the Novel Polyplex Nanoparticle (NP) for Pancreatic Cancer:

The thiol group of thiol—polyethylene glycol-block-poly (L-lysine) (Thiol-PEG-b-PLL) (PEG MW: 5-10,000 g/mol and PLL degree of polymerization=30-50, polydispersity index <1.2) (Alamanda Polymers) is reacted with the maleimide group of maleimide conjugated gastrin-10 peptide (Maleimido-propionyl-Glu-Glu-Glu-Ala-Tyr-Gly-Trp-Met-Asp-Phe-NH2) (Bachem Americas Inc.) at pH 6.5-7, resulting in the formation of a stable thioether linkage between PEG and the gastrin-10 (Ga) peptide to form a gastrin conjugated linear block copolymer, Ga-PEG-b-PLL. The polyplex is prepared by dissolving Ga-PEG-b-PLL in HEPES buffered saline (HBS) (HEPES buffer 20 mM and NaCl 150 mM) (pH 7.4) at various concentrations (N/P ratio of 1, 2 and 5) and slowly mixing with siRNA solution (100 μM in HBS (pH 7.4). The resulting solution is vortexed, and incubated at room temperature for 30 min to allow the formation of the polyplex. The final solution is then filtered using a 0.2 μm filter and stored at mouse and human tissues. The most potent gastrin RNAi: si286-GUGCUGAG-GAUGAGAACUA was used to down regulate gastrin.

Figure 8:
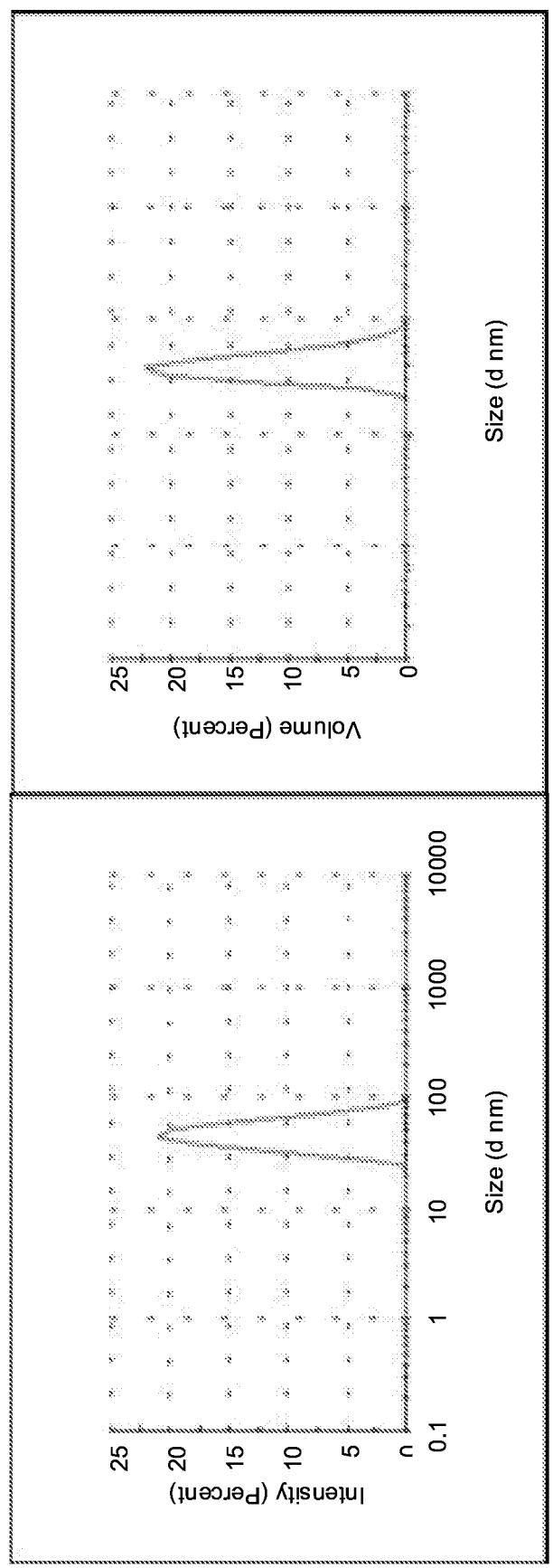
FIG. 8: Size distribution of the untargeted polyplex micelle (N/P ratio 5) by dynamic light scattering (DLS) technique: PEG-PLL block copolymer was complexed with negatively charged gastrin siRNA (si286, GUGCUGAGGAUGAGAACUA) in HEPES buffered saline (HEPES 20 mM and NaCl 150 mM).
Figure 9:
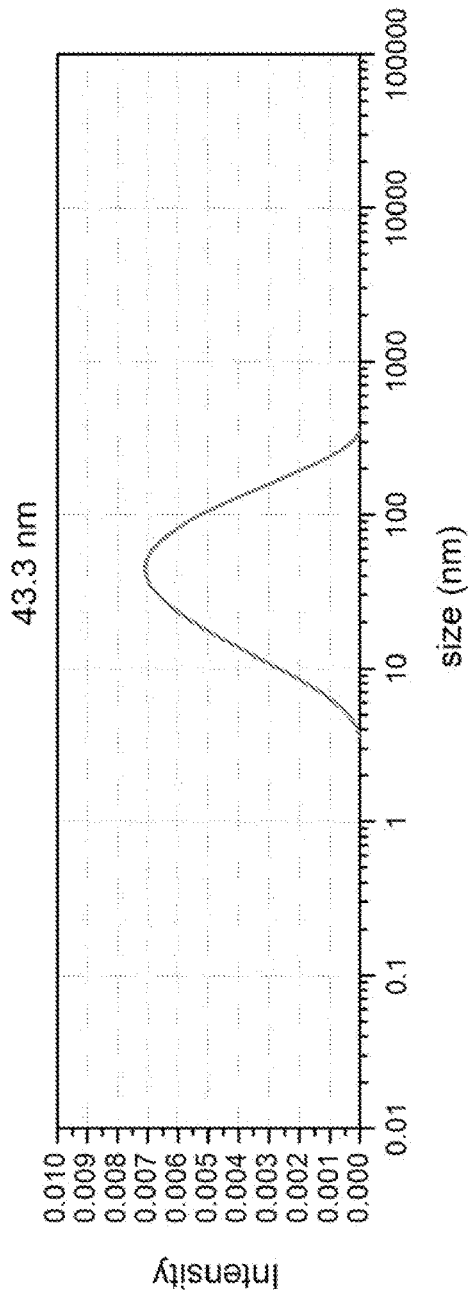
FIG. 9 is a graph showing the reproducibility and stability of the nanoparticles and the ability to form the same size micelle at another center (Georgetown vs NCI (FIG. 8). The particles are 44.3 nm in size making them smaller than many other decorated nanoliposomes hence with less toxicity.
Figure 10:
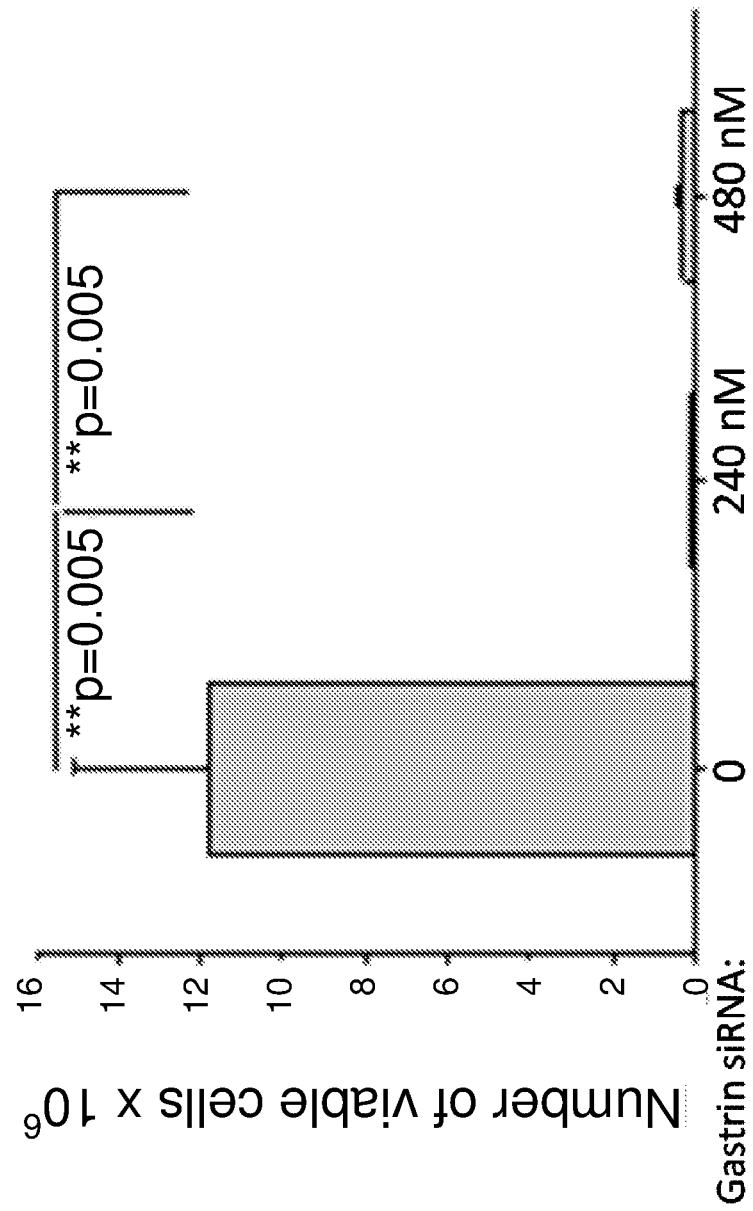
FIG. 10 is a graph showing the results of human pancreatic cancer cells treated in cell culture with 2 different concentrations of nanoparticles couple with siRNA and viable cells counts were done after 48 hrs of exposure. Compared to PBS treated controls selective siRNA NPs significantly inhibited cell growth.
Figure 11:
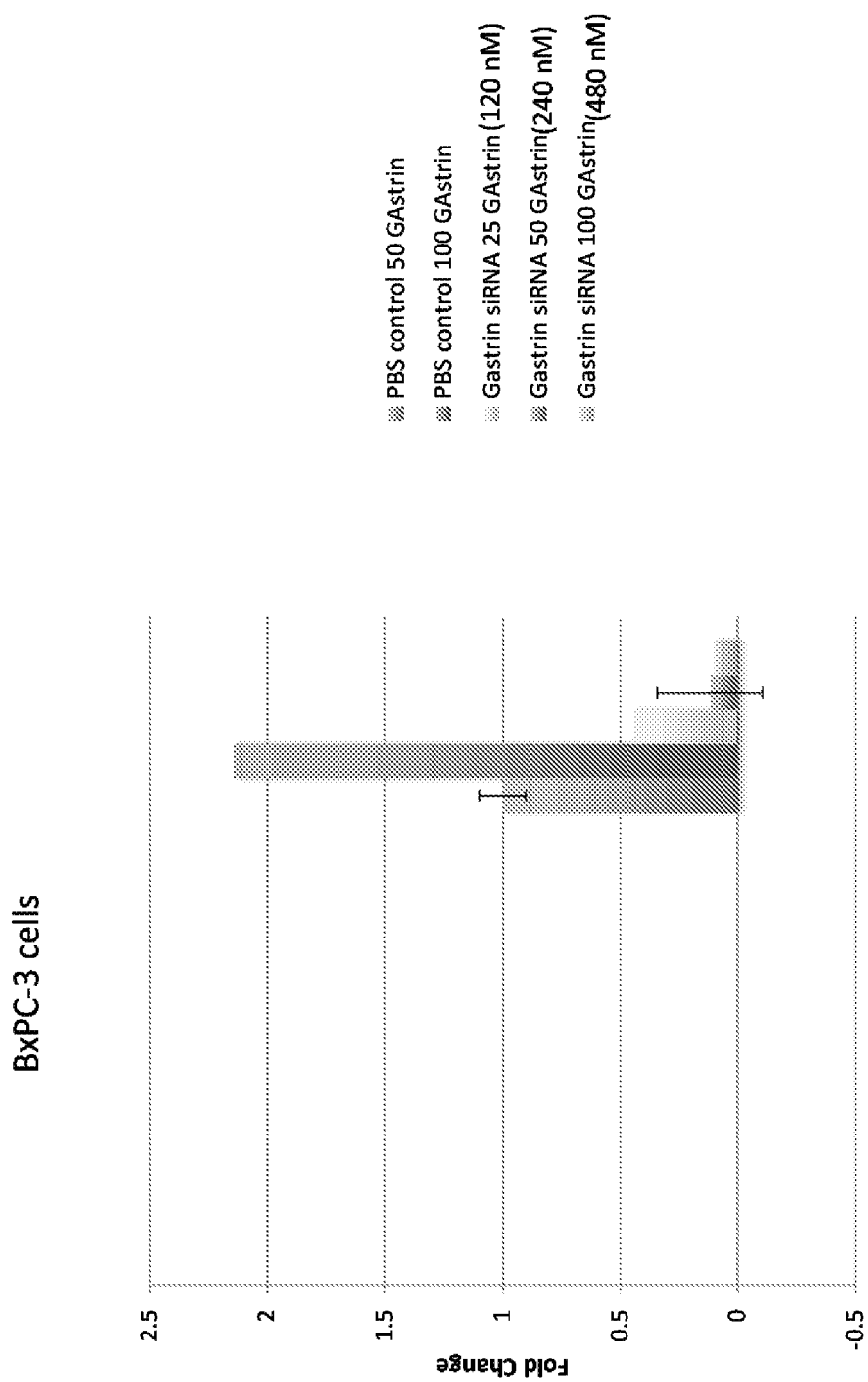
FIG. 11 is a graph showing the results of human pancreatic cancer cells treated in culture with different concentrations of nanoparticles targeted with gastrin siRNA or PBS controls. After 48 hrs the RNA was extracted from the cancer cells and evaluated by quantitative RT-PCR (reverse transcriptase polymerase chain reaction). The data shows that the NPs significantly inhibited gastrin mRNA expression.
Figure 12A:
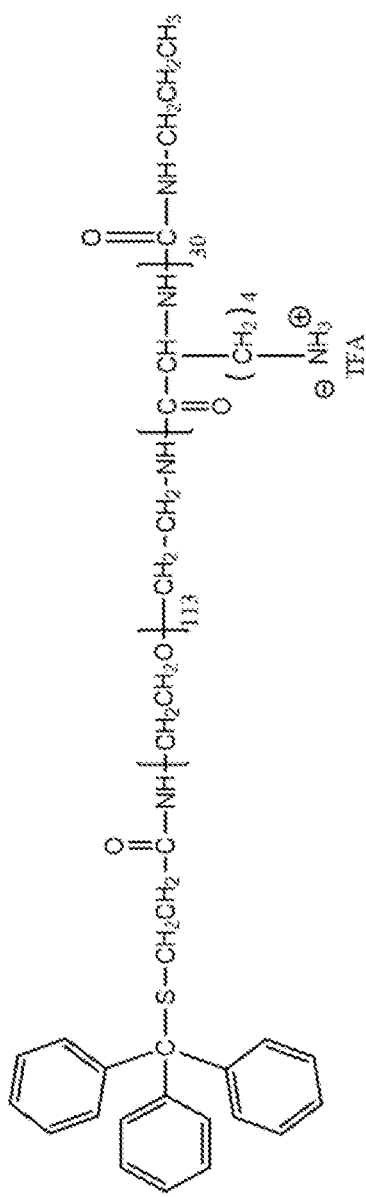
Figure 12D:
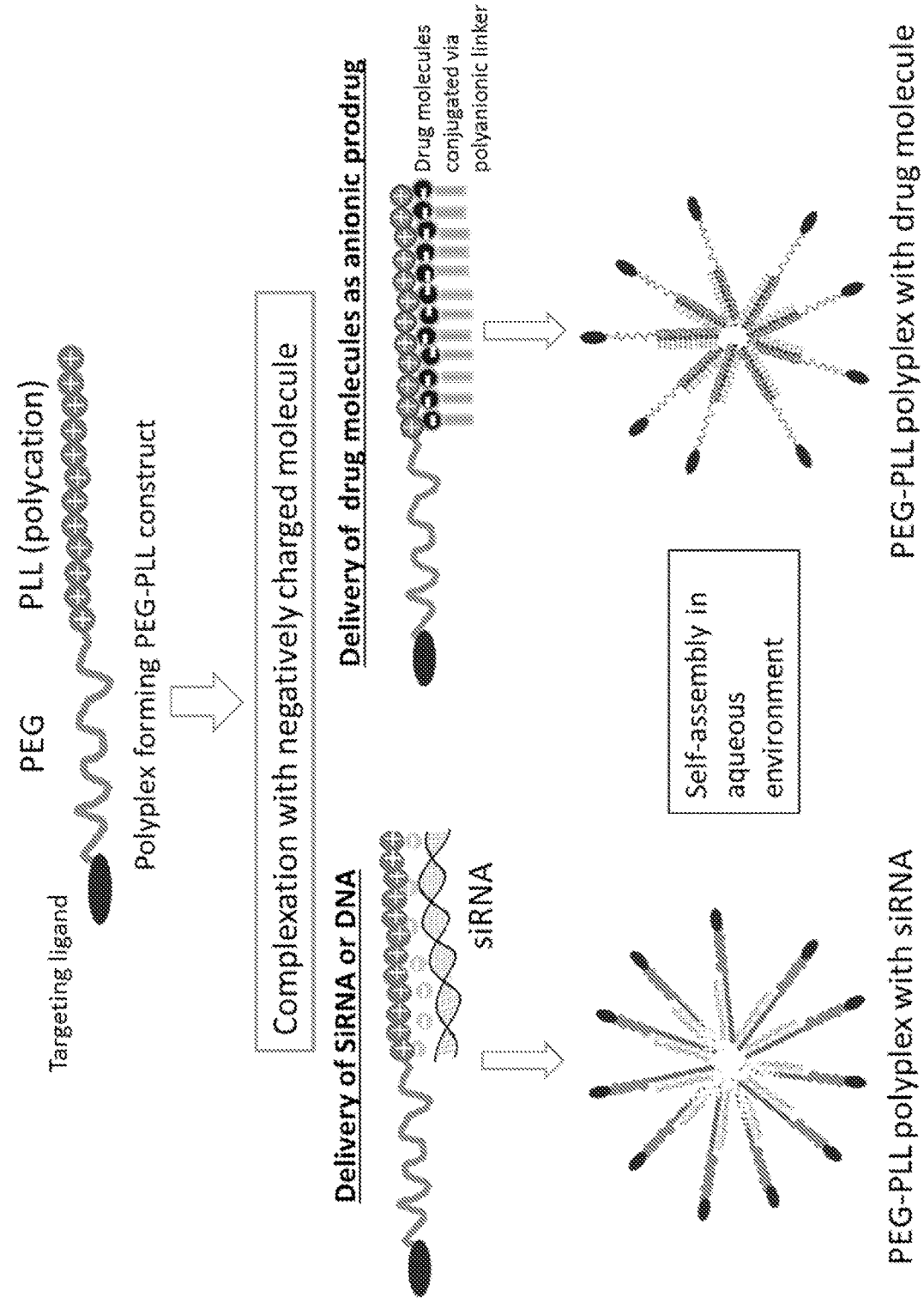

Polyplex NP Characterization:

FIG. 8 demonstrates data on the developed untargeted polyplex micelle showing the ability to measure the NP size with DLS. Size distribution and zeta potential of the complexed NPs is shown in Table 2 showing consistency of size distribution with different N/P rations of nanoparticles.

TABLE 2

Size distribution data of untargeted PEG-PLL/siRNA polyplex micelle at various N/P ratios:

| Polyplex micelle | N/P ratio | Z average (d · nm) | Int. Peak (nm ± SD) | % Int. | Vol. Peak (nm ± SD) | % Int. |
|---|---|---|---|---|---|---|
| PEG-PLL/si286 siRNA | 5 | 44.7 ± 0.2 | <0.1 | 47.4 ± 0.4 | 100 | 42.9 ± 0.3 | 100 |
| PEG-PLL/si286 siRNA | 2 | 46.2 ± 0.6 | <0.1 | 48.5 ± 0.7 | 100 | 40.1 ± 0.4 | 100 |

In Vitro Studies and Cell Line Rationale:

We examined the ability of the polymer-siRNA polyplexes to serve as cancer therapeutic agents in vitro. In our laboratory we maintain several human pancreatic cancer cell lines that represent the range of differentiation (well to poorly differentiated; Table 3), CCK receptor expression, and K-Ras mutant status we expect in human subjects. Cell uptake and IC50-90 will be evaluated by treating pancreatic cancer cells with polyplex NP loaded with fluorescent AlexaFluor 488 (Life Technologies) tagged siRNAs to gastrin or K-Ras and imaged by confocal microscopy (see FIG. 4). Cell characteristics are shown below.

TABLE 3

Characterizations of pancreatic cancer cell lines to be studied in Aim #1

| Cell Line H (human)/ M (murine) | Histologic Differentiation | Endogenous gastrin mRNA conc by qRT-PCR | CCK receptor Expression | KRAS mutation |
|---|---|---|---|---|
| Panc-1 (H) | Poorly | Low | High | Yes |
| BxPC-1 (H) | Well | High | Low | No |
| AsPC-1 (H) | Moderate | Very High | Moderate | Yes |

Cell Proliferation Experimental Methods:

In the cell proliferation assays (Table 4), cancer cells have been treated with the following: gastrin siRNA polyplex NP, K-ras siRNA polyplex NP, (and gastrin siRNA and K-ras siRNA combined), scrambled siRNA polyplex NP controls, and no treatment control. Cells were grown in 12-well plates and treated with siRNA NPs or controls for 48 and 72 hrs. Fresh media and treatments will occur daily. Cells viability and replication will be determined by the trypan blue exclusion or BrdU incorporation assays, respectively. Cell growth will also be measured by the MTS proliferation assay as is done routinely in our laboratory.

TABLE 4

Methods for evaluating cancer cell growth/proliferation and effectiveness of polyplex NPs

| | |
|---|---|
| Cell Counting | 20,000 cells were grown in 12-well tissue culture plates and treated for 48 hrs with polyplex NPs loaded with Kras or gastrin siRNA. Cells were stained for viability with trypan blue and live cells will be counted manually with a hemocytometer. IC50 and IC90 were also calculated in treated PDAC. |
| MTS Assay | 5,000-10,000 cells were plated in 96-well plates and treated with polyplex NPs or controls for 48 hrs. Proliferation was analyzed by colorimetric MTS assay, with the absorbance read at 490 nm. |

Evaluation of Gastrin Knockdown or K-Ras Knockdown by Polyplex NPs:

The efficiency of gastrin gene expression down regulation by polyplex NP treatment was evaluated using quantitative RT-PCR. PCR amplification and analysis were done with the Applied Biosystems Sequence Detection System 7300. Relative gene expression of gastrin was calculated using the AACt method, following the manufacturer's instructions. At least four replicates were performed. Gastrin peptide knockdown was also confirmed with immunofluorescence as shown above in FIG. 5.

KRAS point mutations at codon 12 (from GGT to GAT, or to GTT and, more rarely, to CGT) occur in 75 to 95% of PDAC, a frequency not encountered in any other solid neoplasm. For the Kras studies we used cell line PANC-1 that has the mutated $12^{th}$ codon G→D. The following primers were used for qRT-PCR for Kras: 5'-ACT GGG-GAGGGCTTTCTTTG-3' and 5'-GGCATCAT-CAACACCCTGTCT-3'.

Examine the Ability of Target-Specific siRNA Loaded Polyplex NPs to Safely and Selectively Inhibit Growth and Metastasis of Pancreatic Cancer In Vivo.

Two animal models were used to test the ability of the siRNA loaded polyplex NPs to suppress pancreatic cancer growth: 1) athymic nude mice bearing human BxPC-3 orthotopic pancreatic cancer, and 2) PANC-1 orthotopic pancreatic cancer.

Effects of siRNA Loaded Polyplex NPs on Growth of Orthotopic Human Pancreatic Cancers:

All procedures were conducted in accordance with the IACUC guidelines for humane treatment of animals in research. We used cancer cells that are transfected with luciferase in order to monitor growth on a weekly basis with IVIS imaging as previously described. Two models will be used (FIG. 8).

Effects of Gastrin Selective NPs on Growth and Metastases In Vivo.

Figure 13A:
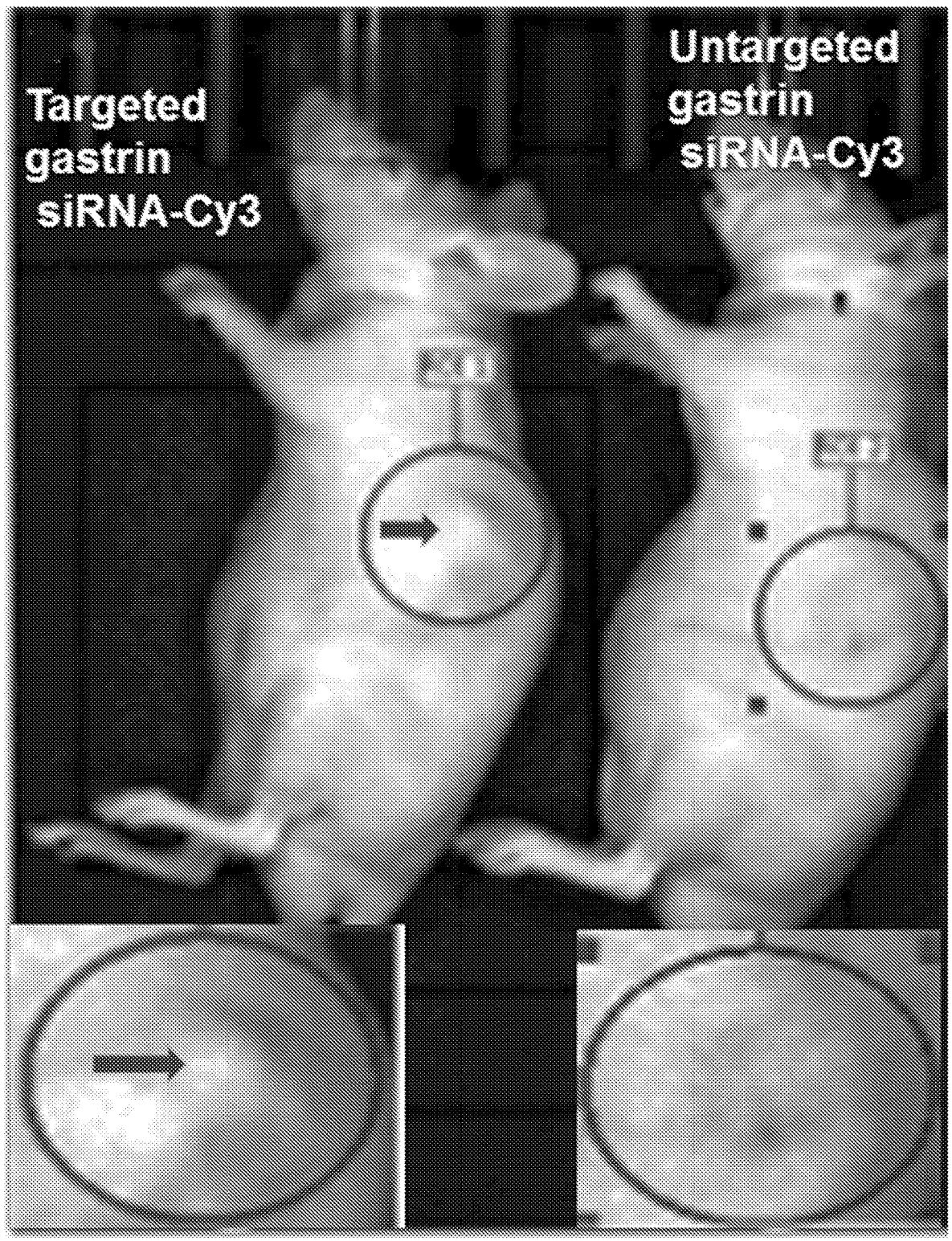
FIGS. 13A-13F. Targeted gastrin siRNA NPs inhibit growth and metastasis of pancreatic cancer in vivo.
Figure 13B:
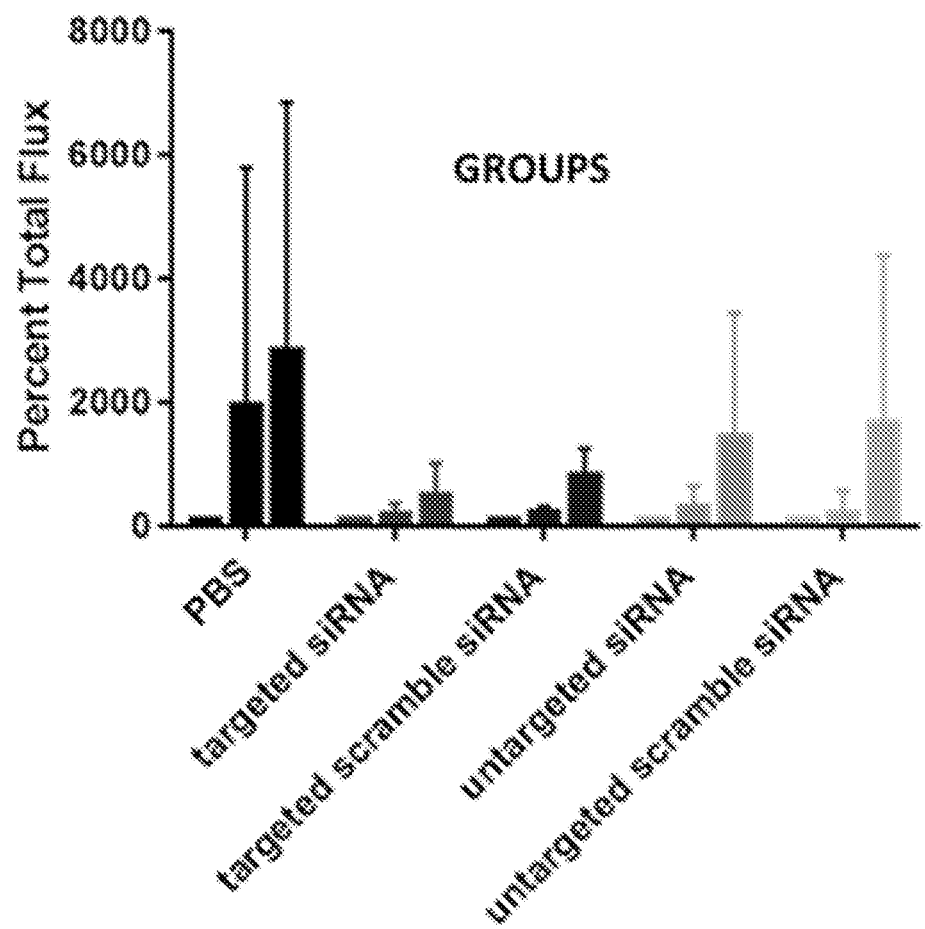
Figure 13C:
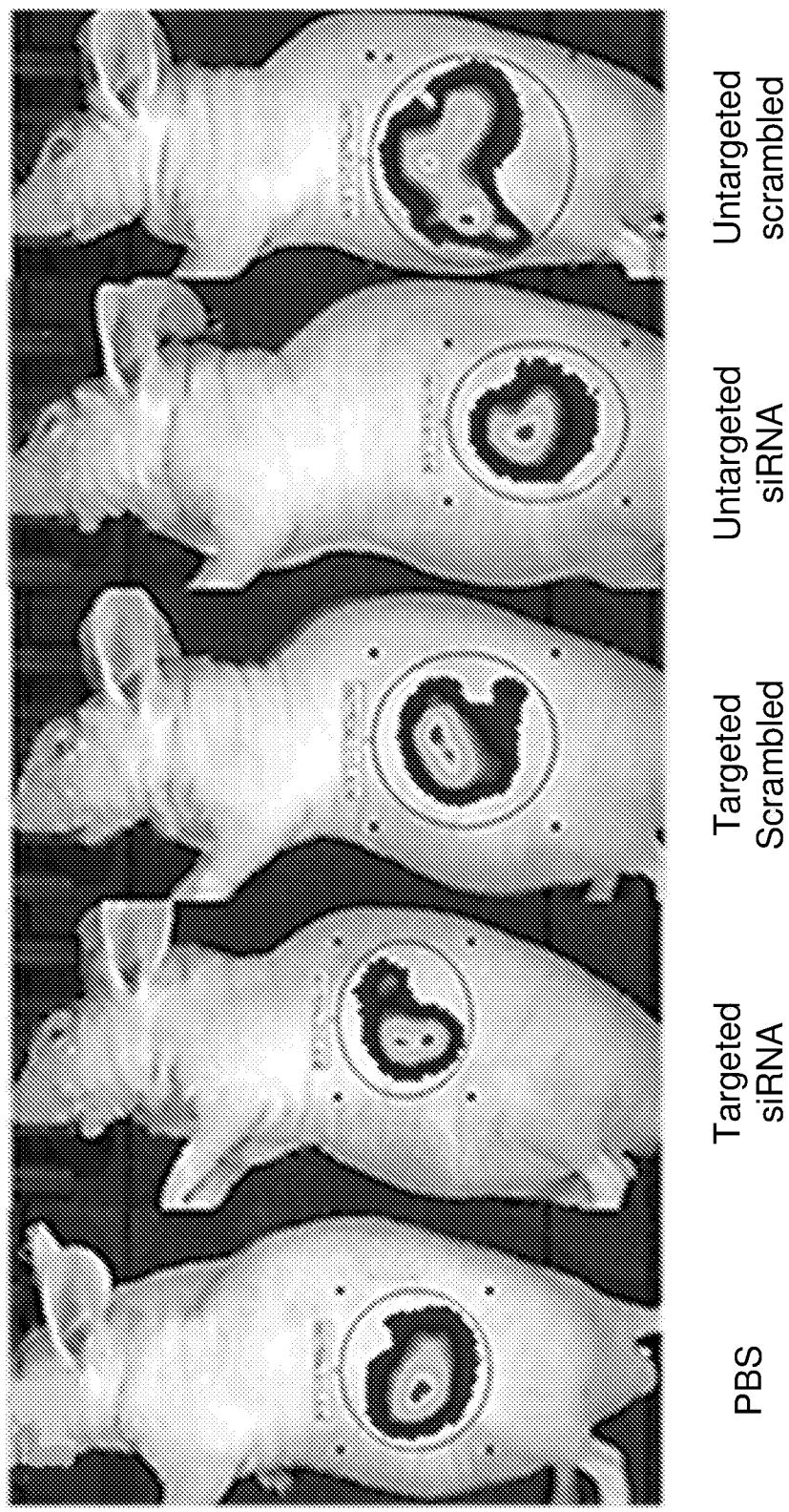
Figure 13D:
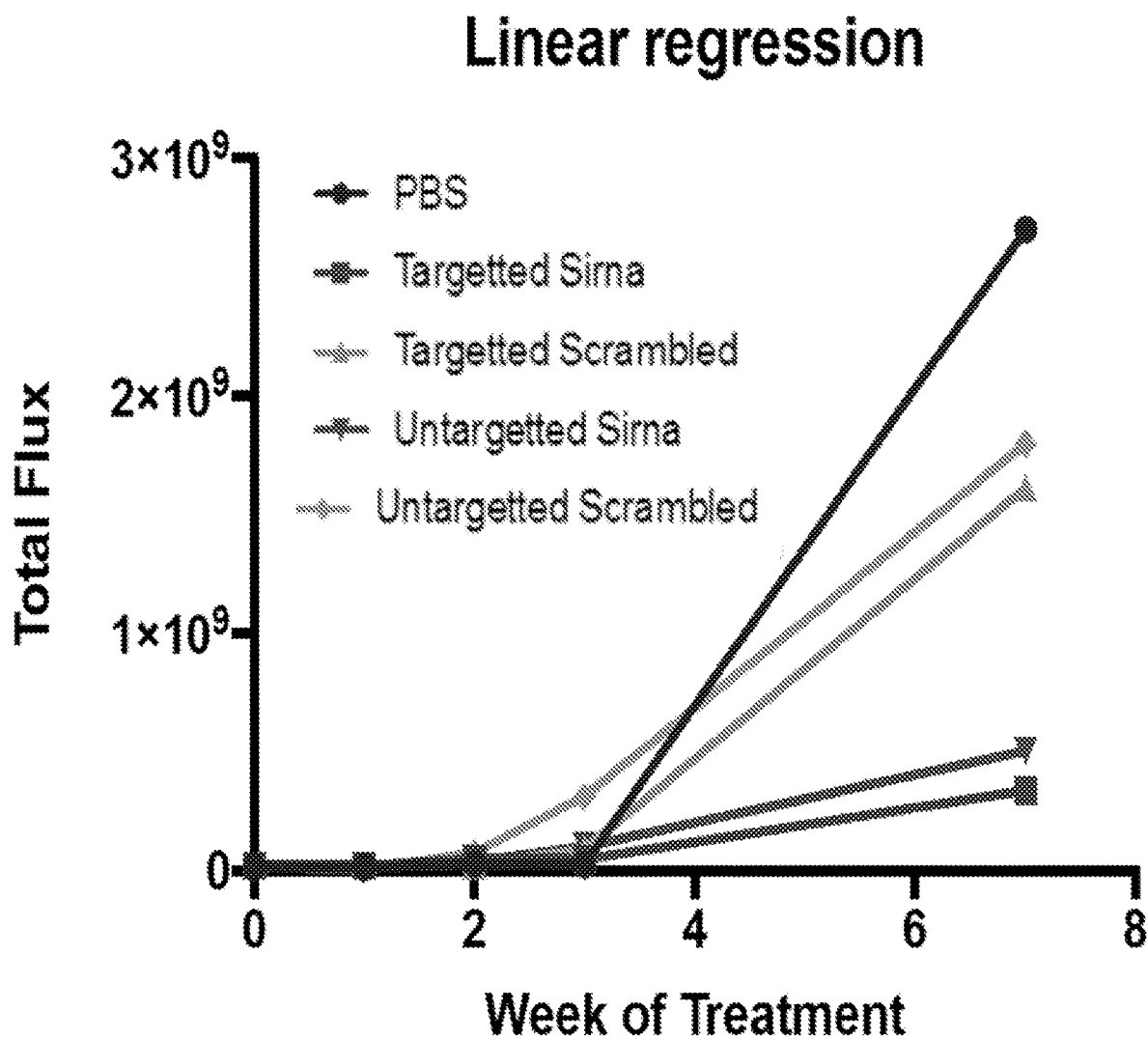
Figure 13E:
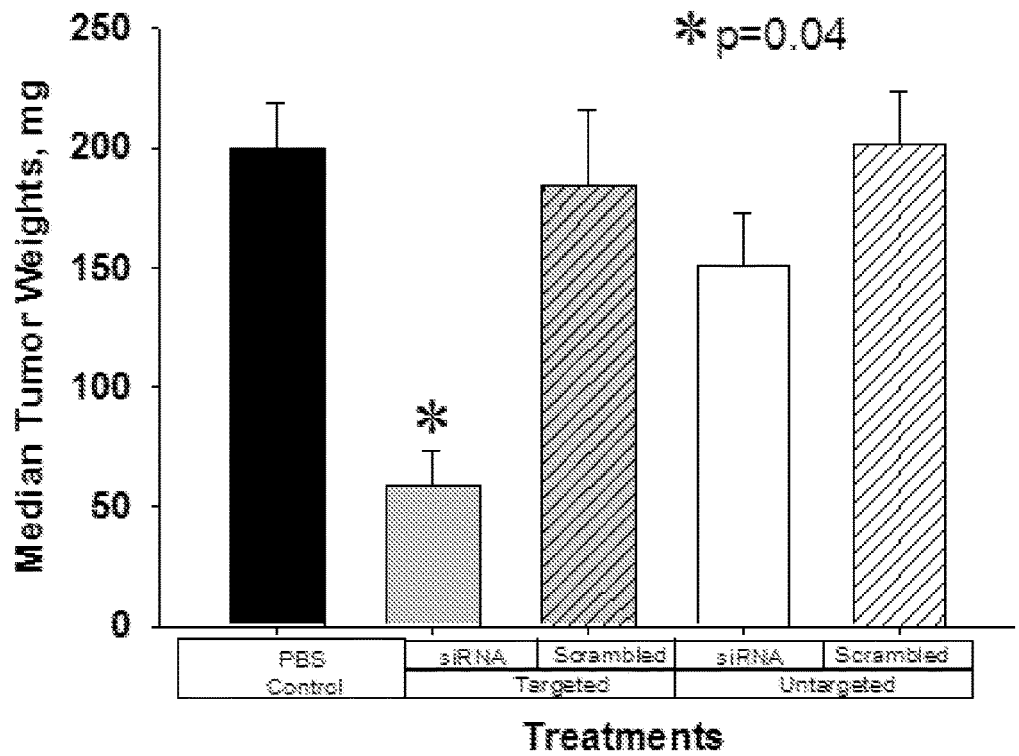
Figure 13F:
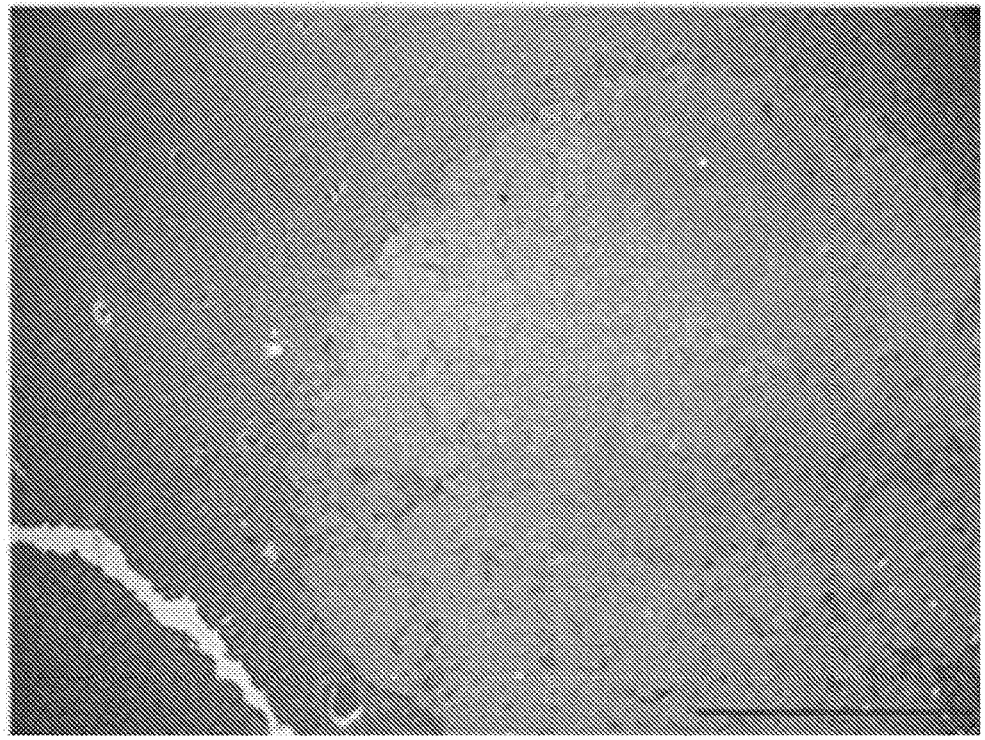

All animal studies were performed in an ethical fashion under a protocol approved by the Georgetown University IACUC board. In order to assure the NPs that were 'targeted' to the CCK-B receptor were taken up into the tumors, we imaged mice were imaged bearing pancreatic cancer orthotopic tumors after intraperitoneal injection of targeted or untargeted Cy3-labeled gastrin siRNA. Fluorescent microscopy showed that uptake by fluorescent imaging was only present in the mice treated with the fluorescent labeled targeted NPs and not the untargeted NPs (FIG. 13A). The growth rate of two different pancreatic cancer cell lines and response to NPs therapy over time was assessed using luciferase tagged human pancreatic cancer cell lines with an IVIS imaging system (Xenogen Corp, Alameda, Calif.). The cells (900,000 for BxPC-3 or $10^6$ for PANC-1) cancer cells were orthotopically implanted into the tail of the pancreas of male athymic nude mice in 100 µl volume. Treatments were all initiated one week after surgical recovery and tumor implantation to assure equal baseline tumor size by the IVIS/luciferase activity assay. Estimated tumor volumes were analyzed by luciferase activity during the study (FIG. 13B). Animals were treated with one of the following three times a week by intraperitoneal injection: PBS/vehicle control, receptor targeted NP-gastrin siRNA, receptor-targeted NP-scrambled control, untargeted NP-gastrin siRNA, and untargeted NP-scrambled control. The concentration of siRNA used to treat the mice bearing BxPC-3 tumors (240 nM) in this experiment showed no statistical differences between the final tumor weights after 4 weeks of therapy. However, none of the mice bearing BxPC-3 tumors had evidence of metastases in the group treated with targeted gastrin siRNA while more than half of the mice in the control groups had metastases in the peritoneum or liver. In the PANC-1 tumor bearing mice, we increased the NP siRNA dose to 480 nM and at this higher dose and the estimated flux by IVIS imaging (FIG. 13C) showed smaller tumor volumes in the mice treated with targeted NPs. The average flux in each group over time showed that targeted NPS had smaller tumor flux (FIG. 13D). The tumors were dissected and weighed from PANC-1 tumor bearing mice and tumor mass was significantly smaller only in the mice treated with targeted gastrin siRNA NPs compared to all the other treatment groups (FIG. 13E). Similar to the mice bearing BxPC-3 tumors, there were also no metastases in the PANC-1 tumor bearing mice when treated with targeted gastrin siRNA NPs, The other PANC-1 control groups exhibited either metastases to the liver (FIG. 13F) or direct invasion to the spleen.

These results show that in an animal model bearing human pancreatic cancer tumors that the NPs that are targeted to selectively bind to the CCK-B receptor concentrate in the orthotopic tumors more efficiently than untargeted NPs. In both murine models of pancreatic cancer, only the targeted NPs with gastrin siRNA prevented metastases.

Mechanism of Action for the Impaired Tumor Growth and Metastases with Target-Specific siRNA Loaded NPs.

The reason why the targeted NPs were more effective in decreasing PANC-1 primary tumor growth and preventing metastases in both cancers is most likely related to the enhanced tumor uptake rendered by making the NPs selective to bind to the CCK-B receptor on the cancer cells (as demonstrated by the Cy3 fluorescent uptake (FIGS. 13A and 13B). Tumors were sectioned and evaluated for gastrin by immunohistochemistry to confirm that the gastrin siRNA was indeed down regulating gastrin peptide expression.

Process for making nanoparticle/siRNA constructs:

1. Take out the polymer from freezer and equilibrate at r.t. for ~20 minutes (protected from light)
2. Weigh appropriate amount of Ga-PEG-PLL (1.3 mg) polymer in a vial and dissolve in Rnase free PBS (1×).
3. Dissolve the total siRNA in 800 µL of Rnase free PBS (1×) to obtain the concentration of 100 µM of gastrin siRNA. Dilute the siRNA 5× with Rnase free PBS (1×) to obtain 20 µM working concentration.
4. Mix 800 µL of Ga-PEG-PLL (1.623 mg/mL) with 800 µL of Gastrin siRNA (20 µM) and pipette up and down for mixing the polymer with siRNA (DO NOT VORTEX) and leave for 30 minutes protected from light at RT for complex formation.
5. Measure the size by diluting (10×) the complex in Rnase free PBS. You should obtain a hydrodynamic size of ~45 nm.

| siRNA vs Ga-PEG-PLL complexation ratio: N/P ratio = 5 | | | | | |
| --- | --- | --- | --- | --- | --- |
| Complexing agent | MW (g/mol) | Working conc. | molar ratio | Mixing volume | Required amount |
| Ga-PEG-PLL | 9,900 | 1.625 mg/mL | 8.2 | 800 µL | 1.3 mg |
| Gastrin siRNA | 16,100 | 20 µM | 1 | 800 µL | 16 nM |

In view of the many possible embodiments to which the principles of the disclosed compositions and methods may be applied, it should be recognized that the illustrated embodiments are only preferred examples of the invention and should not be taken as limiting the scope of the invention.

What is claimed is:

1. A construct, or a pharmaceutically acceptable salt thereof, comprising:
   (a) a polyethylene glycol-block-poly(L-lysine) polymer moiety, wherein the polyethylene glycol is thiol-functionalized;
   (b) a cholecystokinin-B (CCK-B) receptor ligand coupled to the polyethylene glycol of the polymer moiety; and
   (c) a siRNA complexed with the poly(L-lysine) of the polymer moiety, wherein the construct is neutralized.

2. The construct of claim 1, wherein the construct is a nanoparticle having an average hydrodynamic size (Z Ave 48 nm) of less than 100 nm.

3. The construct of claim 1, wherein the construct is a nanoparticle having an average hydrodynamic size (Z Ave 48 nm) of 30 to 60 nm.

4. The construct of claim 1, wherein the siRNA is a GASTRIN-targeted siRNA, a mutant KRAS-targeted siRNA, or a combination thereof.

5. The construct of claim 1, wherein the cholecystokinin-B (CCK-B) receptor ligand comprises gastrin-10.

6. The construct of claim 1, wherein the cholecystokinin-B (CCK-B) receptor ligand comprises a DNA aptamer.

7. The construct of claim 1, wherein the cholecystokinin-B (CCK-B) receptor ligand has a structure of 3-maleimido-propionyl-Glu-Glu-Glu-Ala-Tyr-Gly-Trp-Met-Asp-Phe-NH$_2$.

8. The construct of claim 1, wherein the (a) and (b) moieties of the construct together have a structure of:

Gastrin 10—N(maleimide)—S—(CH$_2$CH$_2$O)$_x$—CH$_2$CH$_2$NH—[C(=O)—CH(—(CH$_2$)$_4$—NH$_3^+$ Cl$^-$)—NH]$_y$—H wherein x is 22 to 454, more particularly 45 to 275; and y is 10 to 200, more particularly 20 to 50.

9. The construct of claim 1, wherein the (a) and (b) moieties of the construct together have a structure of:

Y—X—PEG—CH$_2$CH$_2$NH—[C(=O)—CH(—(CH$_2$)$_4$—NH$_3^+$ Cl$^-$)—NH]$_y$—H wherein Y is the cholecystokinin-B (CCK-B) receptor ligand; X is a linker; PEG is polyethylene glycol; and y is 10 to 200, more particularly 20 to 50.

10. The construct of claim 1, wherein the siRNA is selected from:

GUGCUGAGGAUGAGAACUA;  (SEQ ID NO: 1)

GAUGCACCCUUAGGUACAG;  (SEQ ID NO: 2)
or
AGAAGAAGCCUAUGGAUGG.  (SEQ ID NO: 3)

11. The construct of claim 1, wherein the construct comprises a polyplex structure having the siRNA in a core surrounded by the polyethylene glycol, wherein the cholecystokinin-B (CCK-B) receptor ligand is located on the surface of the polyplex structure.

12. The construct of claim 6, wherein the DNA aptamer comprises, or consists of:

```
                                          (SEQ. ID No: 4)
CATGGTGCAG GTGTGGCTGG GATTCATTTG CCGGTGCTGG
TGCGTCCGCG GCCGCTAATC CTGTTC.
```

13. A construct, or a pharmaceutically acceptable salt thereof, comprising:
   (a) a polyethylene glycol-block-poly(L-lysine) polymer moiety, wherein the polyethylene glycol is thiol-functionalized;
   (b) a cholecystokinin-B (CCK-B) receptor ligand coupled to the polyethylene glycol of the polymer moiety; and
   (c) a therapeutically active agent complexed with the poly(L-lysine) of the polymer moiety,
   wherein the construct is neutralized.

14. The construct of claim 13, wherein the therapeutically active agent is selected from a siRNA, collagen peptide, a cell adhesion molecule, an intracellular signaling protein, or a KRAS downstream effector.

15. A pharmaceutical composition comprising at least one pharmaceutically acceptable additive and at least one construct of claim 1.

16. A method of treating a cancer that possesses a CCK-B receptor in a subject comprising administering to the subject in need thereof a therapeutically effective amount of the construct of claim 1, wherein the siRNA is GASTRIN-targeted, and wherein the cancer is pancreatic cancer, colorectal cancer, gastric cancer, distal esophageal adenocarcinoma, medullary thyroid cancer, small cell lung cancer, or carcinoid tumors.

17. The method of claim 16, wherein the cancer is pancreatic cancer.

18. The method of claim 17, wherein the pancreatic cancer is pancreatic ductal adenocarcinoma.

19. The method of claim 16, wherein the method is selective for treating pancreatic cancer.

20. The method of claim 16, wherein the treating comprises inhibiting metastasis of the cancer.

21. The construct of claim 1, wherein the siRNA is a GASTRIN-targeted siRNA.

22. The construct of claim 9, wherein X is a thioether.

23. The construct of claim 21, wherein the cholecystokinin-B (CCK-B) receptor ligand comprises gastrin-10.

24. The construct of claim 13, wherein the cholecystokinin-B (CCK-B) receptor ligand comprises gastrin-10.

25. The construct of claim 13, wherein the (a) and (b) moieties of the construct together have a structure of:

$$Y-X-PEG-CH_2CH_2NH-\left(\underset{\underset{(CH_2)_4}{\underset{|}{|}}}{\overset{H}{\underset{|}{C}}}-\overset{H}{\underset{|}{C}}-\overset{H}{\underset{|}{N}}\right)_y H \quad NH_3^{\oplus} \ Cl^{\ominus}$$

wherein Y is the cholecystokinin-B (CCK-B) receptor ligand; X is a linker; PEG is polyethylene glycol; and y is 10 to 200, more particularly 20 to 50.

26. The construct of claim 25, wherein X is a thioether.

27. The construct of claim 13, wherein the construct comprises a polyplex structure having the therapeutic agent in a core surrounded by the polyethylene glycol, wherein the cholecystokinin-B (CCK-B) receptor ligand is located on the surface of the polyplex structure.

28. The method of claim 16, wherein the construct comprises a polyplex structure having the siRNA in a core surrounded by the polyethylene glycol, wherein the cholecystokinin-B (CCK-B) receptor ligand is located on the surface of the polyplex structure.

29. The method of claim 16, wherein the cholecystokinin-B (CCK-B) receptor ligand comprises gastrin-10.

30. The method of claim 16, wherein the (a) and (b) moieties of the construct together have a structure of:

$$Y-X-PEG-CH_2CH_2NH-\left(\underset{\underset{(CH_2)_4}{\underset{|}{|}}}{\overset{H}{\underset{|}{C}}}-\overset{H}{\underset{|}{C}}-\overset{H}{\underset{|}{N}}\right)_y H \quad NH_3^{\oplus} \ Cl^{\ominus}$$

wherein Y is the cholecystokinin-B (CCK-B) receptor ligand; X is a linker; PEG is polyethylene glycol; and y is 10 to 200, more particularly 20 to 50.

31. The method of claim 17, wherein the construct comprises a polyplex structure having the siRNA in a core surrounded by the polyethylene glycol, wherein the cholecystokinin-B (CCK-B) receptor ligand is located on the surface of the polyplex structure.

32. The method of claim 17, wherein the cholecystokinin-B (CCK-B) receptor ligand comprises gastrin-10.

33. The method of claim 17, wherein the (a) and (b) moieties of the construct together have a structure of:

$$Y-X-PEG-CH_2CH_2NH-\left(\underset{\underset{(CH_2)_4}{\underset{|}{|}}}{\overset{H}{\underset{|}{C}}}-\overset{H}{\underset{|}{C}}-\overset{H}{\underset{|}{N}}\right)_y H \quad NH_3^{\oplus} \ Cl^{\ominus}$$

wherein Y is the cholecystokinin-B (CCK-B) receptor ligand; X is a linker; PEG is polyethylene glycol; and y is 10 to 200, more particularly 20 to 50.

\* \* \* \* \*